(12) United States Patent
Park et al.

(10) Patent No.: US 12,018,279 B2
(45) Date of Patent: Jun. 25, 2024

(54) MICRO-ENGINEERED MODELS OF THE HUMAN EYE AND METHODS OF USE

(71) Applicant: THE TRUSTEES OF THE UNIVERSITY OF PENNSYLVANIA, Philadelphia, PA (US)

(72) Inventors: Sunghee Estelle Park, Philadelphia, PA (US); Wenli Yang, Media, PA (US); Dwight E. Stambolian, Monroeville, NJ (US); Dongeun Huh, Villanova, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 214 days.

(21) Appl. No.: 17/074,074

(22) Filed: Oct. 19, 2020

(65) Prior Publication Data

US 2021/0115400 A1 Apr. 22, 2021

Related U.S. Application Data

(60) Provisional application No. 62/923,419, filed on Oct. 18, 2019.

(51) Int. Cl.
| | | |
|---|---|---|
| *C12N 5/079* | (2010.01) | |
| *C07K 14/47* | (2006.01) | |
| *C07K 14/52* | (2006.01) | |
| *C07K 14/75* | (2006.01) | |

(52) U.S. Cl.
CPC .......... *C12N 5/0621* (2013.01); *C07K 14/472* (2013.01); *C07K 14/52* (2013.01); *C07K 14/75* (2013.01); *C12N 2500/05* (2013.01); *C12N 2513/00* (2013.01)

(58) Field of Classification Search
CPC .............. C12N 5/0621; C12N 2500/05; C12N 2513/00; C12N 5/062; C12N 5/0062; C07K 14/472; C07K 14/52; C07K 14/75
See application file for complete search history.

(56) References Cited

U.S. PATENT DOCUMENTS

| | | |
|---|---|---|
| 5,045,694 A | 9/1991 | Beavis et al. |
| 5,118,937 A | 6/1992 | Hillenkamp et al. |
| 5,322,770 A | 6/1994 | Gelfand |
| 6,329,209 B1 | 12/2001 | Wagner et al. |
| 6,365,418 B1 | 4/2002 | Wagner et al. |
| 6,379,897 B1 | 4/2002 | Weidenhammer et al. |

(Continued)

OTHER PUBLICATIONS

Achberger et al, Human Retina-on-a-Chip: Merging Organoid and Organ-on-a-Chip Technology to Generate Complex Multi-Layer Tissue Models. doi: 10.1101/552158. Posted on BioRxiv Feb. 18, 2019. Retrieved from www.biorxiv.org/content/10.1101/552158v1.full. Retrieved on Aug. 25, 2022. (Year: 2019).*

(Continued)

*Primary Examiner* — Arthur S Leonard
*Assistant Examiner* — Jianjian Zhu
(74) *Attorney, Agent, or Firm* — BakerHostetler

(57) ABSTRACT

This present disclosure relates to a bioengineering approach based on microphysiological culture to mimic tissue-tissue interface. Accordingly, the present disclosure provides methods, compositions and kits related to the approach.

12 Claims, 31 Drawing Sheets
(31 of 31 Drawing Sheet(s) Filed in Color)

(56) References Cited

U.S. PATENT DOCUMENTS

| | | |
|---|---|---|
| 6,451,536 B1 | 9/2002 | Fodor et al. |
| 6,548,257 B2 | 4/2003 | Lockhart et al. |
| 6,618,679 B2 | 9/2003 | Loehrlein et al. |
| 6,664,377 B1 | 12/2003 | Xu |
| 2002/0155493 A1 | 10/2002 | Wang |
| 2003/0013208 A1 | 1/2003 | Jendoubi |
| 2003/0017515 A1 | 1/2003 | Ye et al. |
| 2003/0077616 A1 | 4/2003 | Lomas |
| 2003/0134304 A1 | 7/2003 | Van Der et al. |
| 2003/0157485 A1 | 8/2003 | Bejanin et al. |
| 2003/0199001 A1 | 10/2003 | Pitt et al. |
| 2003/0215858 A1 | 11/2003 | Templeton |
| 2019/0290803 A1 | 9/2019 | Bharti et al. |

OTHER PUBLICATIONS

Chung et al., 2018. Wet-AMD on a Chip: Modeling Outer Blood-Retinal Barrier In Vitro. Adv. Healthcare Mater. 7(2), 1700028. doi: 10.1002/adhm.201700028. Supplemental Figures (Year: 2018).*

Bergman, "Ladder Sequencing," Proteomics in Functional Genomics 88: 133-144 (2000).

Chait et al., "Protein Ladder Sequencing," Science 262(5130):89-92 (1993).

Gerhold et al., "DNA chips: promising toys have become powerful tools," Trends in Biochem. Sci. 24:168-173 (1999).

Huh et al., "Microfabrication of human organs-on-chips," Nature Protocols 8(11):2135-2157 (2013).

Keough et al., "A method for high-sensitivity peptide sequencing using postsource decay matrix-assisted laser desorption ionization mass spectrometry," Proc. Natl. Acad. Sci. USA. 96:7131-7136 (1999).

Kirk-Othmer Encyclopedia of Chemical Technology, 4th ed. vol. 15 (John Wiley & Sons, New York 1995), pp. 1071-1094.

Kuster et al., "Identifying proteins and post-translational modifications by mass spectrometry," Curr. Opin. Structural Biol 8:393-400 (1998).

Lennon et al., "High-throughput gene expression analysis for drug discovery," DDT 5(2):59-65 (2000).

Li et al., "Single-cell MALDI: a new tool for direct peptide profiling," Tibtech 18: 151-160 (2000).

Marshall et al., "Detection of HCV RNA by the Asymmetric Gap Ligase Chain Reaction," PCR Methods and Applications 4:80-84 (1994).

Rowley et al., "Applications of Protein Mass Spectrometry in Cell Biology," Methods 20:383-397 (2000).

Schena et al., "Quantitative Monitoring of Gene Expression Patterns with a Complementary DNA Microarray," Science 20:467-470 (1995).

Towbin et al., "Electrophoretic transfer of proteins from polyacrylamide gels to nitrocellulose sheets: Procedure and some applications," Proc. Nat. Acad. Sci. USA 76(9):4350-4354 (1979).

Achberger, K. et al., "Merging organoid and organ-on-a-chip technology to generate complex multi-layer tissue models in a human retina-on-a-chip platform," eLife, vol. 8, No. e46188, Aug. 2019, pp. 1-26.

Arik, Y.B., et al., Microfluidic organ-on-a-chip model of the outer blood-retinal barrier with clinically relevant read-outs for tissue permeability and vascular structure, Lab Chip, vol. 21, No. 2, Jan. 21, 2021, pp. 272-283.

Chen, L-J., et al., "Microfluidic co-cultures of retinal pigment epithelial cells and vascular endothelial cells to investigate choroidal angiogenesis," Scientific Reports, vol. 7, No. 3538, Jun. 14, 2017, pp. 1-9.

Chung, M., et al., "Wet-AMD on a Chip: Modeling Outer Blood-Retinal Barrier In Vitro," Advanced Healthcare Materials, vol. 7, No. 2, Jan. 2018, pp. 1-7.

Ghareeb, A.E., et al., "Coculture techniques for modeling retinal development and disease, and enabling regenerative medicine," Stem Cells Transl Med., vol. 9, No. 12, Dec. 2020, pp. 1531-1548.

Jeon, J., et al., "Tissue Engineered Human Blood-Retinal Barrier-on-a-Chip," ARVO Annual Meeting Abstract, vol. 57, No. 5325, Sep. 2016.

Manian, K.V., et al., "3D iPSC modeling of the retinal pigment epithelium-choriocapillaris complex identifies factors involved in the pathology of macular degeneration," Cell Stem Cell, vol. 28, No. 5, May 6, 2021, pp. 846-862.

Paek et al., "Microphysiological Engineering of Self-Assembled and Perfusable Microvascular Beds for the Production of Vascularized Three-Dimensional Human Microtissues", ACS Nano., Jul. 23, 2019, vol. 13, No. 7, 7627-7643.

* cited by examiner

MICRO-ENGINEERED MODELS OF THE HUMAN EYE AND METHODS OF USE

CROSS-REFERENCE TO RELATED APPLICATIONS

This application is a U.S. patent application which claims priority to U.S. Provisional Patent Application Ser. No. 62/923,419, filed on Oct. 18, 2019, the contents of each of which are incorporated by reference herein in their entirety.

STATEMENT REGARDING FEDERALLY FUNDED RESEARCH

This invention was made with government support under grant number 1DP2HL127720-01 awarded by NIH. The government has certain rights in this invention.

BACKGROUND

Age-related macular degeneration (AMD) is a leading cause of visual impairment and blindness in people over the age of 60, with more than 200,000 US cases per year. Visual dysfunction in AMD is associated with the degeneration of retinal pigmented epithelium (RPE) cells that begins with impaired clearance of cellular waste material. This leads to a state of chronic inflammation in the eye in addition to the formation of abnormal deposits underneath RPE cells called drusen, which impair the function of RPE cells. Despite interest in improving the quality of life of AMD patients, a need remains for clinical treatment of dry AMD, the most common form of the disease.

Certain rodent models have been used for AMD studies, but have limitations to fully mimic characteristics of the human AMD as rodents lack macula in the retina. Studying the pathophysiology of age-related macular degeneration in vitro requires the ability to model the retinal pigment epithelium (RPE)-choroid complex in the outer layer of the retina. However, certain in vitro models do not realistically mimic this important tissue-tissue interface.

A significant impediment to tissue engineering, disease modeling, and drug discovery has been a notable lack of in vitro culture systems that mimic this important tissue-tissue interface. There is a need for a three dimensional (3D) organoid that is broadly applicable to numerous pathological tissues and that recapitulate the in vivo cellular and tissue ultrastructure.

SUMMARY

The present disclosure provides a three dimensional (3D) in vitro organoid including a microfluidic chip; retinal pigment epithelial cells; and perfusable vessels.

In certain embodiments, the microfluid chip includes a first and a second layers. In certain embodiments, the first and second layers include polymidethylsiloxane (PDMS). In certain embodiments, the first layer includes at least one cell culture medium reservoir. In certain embodiments, the at least one reservoir has a diameter of about 6 mm.

In certain embodiments, the retinal pigment epithelial cells are derived from inducible pluripotent stem cells (iPSC).

In certain embodiments, the perfusable vessels have a thickness of about 400 μm. In certain embodiments, the perfusable vessels include encapsulated cells. In certain embodiments, the encapsulated cells are included in an extracellular matrix hydrogel. In certain embodiments, the extracellular matrix hydrogel includes fibrinogen and thrombin (fibrin). In certain embodiments, the encapsulated cells include fibroblasts. In certain embodiments, the encapsulated cells include endothelial cells.

In certain embodiments, the retinal pigment epithelial cells are derived from a subject. In certain embodiments, the subject has age-related macular degeneration (AMD).

The present disclosure also provides methods for identifying a composition that modulates the outer blood-retinal-barrier. In some embodiments, a method includes obtaining retinal pigment epithelial cells from a subject and preparing a three dimensional in vitro organoid that includes the retinal pigment epithelial cells. A test agent is contacted with the organoid, and the test agent that induces at least one biological response identifyed as the composition.

In certain embodiments, the subject has age-related macular degeneration. In certain embodiments, the at least one biological response is selected from the group consisting of RPE65 expression, hypopigmentation, number of drusen-like basal deposits, size of drusen-like basal deposit, laminin expression, collagen expression, phagocytic activity, caspase activity, apoptotic activity, secretion of cytokines, and secretion of complement proteins. In certain embodiments, the secretion of cytokines includes secretion of pigment epithelium-derived factor (PEDF). In certain embodiments, the secretion of cytokines includes secretion of vascular endothelium growth factor (VEGF). In certain embodiments, the secretion of complement proteins includes secretion of C3, CFH, CFI, CD46, CD59, CD5b-9, or any combination thereof.

BRIEF DESCRIPTION OF THE DRAWINGS

For a more complete understanding of the present disclosure and its features and advantages, reference is now made to the following description, taken in conjunction with the accompanying drawings. The patent or application file contains at least one drawing executed in color. Copies of this patent or patent application publication with color drawing(s) will be provided by the Office upon request and payment of the necessary fee.

FIG. 1A illustrates a retinal pigment epithelium (RPE)-choroid complex in the outer layer of the retina. FIG. 1B illustrates a photograph of the oBRB chip. FIG. 1C illustrates a polydimethylsiloxane (PDMS) device. FIGS. 1D-1F illustrate endothelial cells embedded in the ECM hydrogel. FIG. 1G illustrates expression of ZO-1 after 21 days of culture. FIGS. 1G-1J illustrate expression of ZO-1, RPE pigmentation and the production of basal deposits and basement membrane protein.

FIG. 12A illustrates that the anatomical and histological characterization of the retina. FIG. 12B illustrates photograph of the oBRB chip. FIG. 12C illustrates that the device comprises two PDMS layers separated by a porous membrane. FIG. 12D illustrates cell culture procedure to form RPE-choroid complex on a chip. FIG. 12E illustrates RPE65 and CD31 immunostaining. FIG. 12F illustrates immunofluorescence staining of CD31 in co-culture of endothelial cells and fibroblasts in the hydrogel leading to the formation of network structure. FIGS. 12G-12H illustrate imagines of flow of 70 kDa dextran in engineered perfusable vessels FIGS. 12I-12J illustrate barrier integrity and diffusivity in engineered perfusable vessels. FIGS. 12K-12L illustrate denser network in the co-culture of endothelial cells and RPEs as compared with the endothelial monoculture model.

FIG. 13A illustrate a model comprising primary human RPEs co-cultured with endothelial cells to form perfusable vascular network. FIG. 13B illustrate human RPE organized into a epithelial monolayer. FIG. 13C illustrate melanosome staining of RPEs in co-culture with engineered vessels. FIG. 13D illustrate increased number of drusen-like deposits on the basolateral compartment. FIG. 13E illustrate immunostaining of laminin accumulated on the basolateral side of the epithelium. FIG. 13F illustrate intercellular tight junctions (ZO-1) after 21 days of RPEs co-cultured with vessels. FIG. 13G illustrate time-course measurement of diffused fluorescein intensity in co-culture of RPEs and vessels. FIG. 13H illustrate the phagocytic activity of RPEs with higher fluorescence intensity of pHrodo-labeled bacteria in phagosomes of RPE.

FIG. 14A shows RPEs differentiated from an iPS cell line obtained from a healthy donor. FIG. 14B shows iPSC-derived RPEs forming a confluent epithelial monolayer, tight junction formation and phagocytic activity. FIG. 14C shows melanosome immunostaining of iPSC-RPEs cultured on BRB chip. FIG. 14D shows immunostaining of APOE. FIGS. 14E-14F show barrier function and phagocytic function in iPSC-RPEs. FIGS. 14G-14H show co-culture of iPSC-RPEs and endothelial cells with similar vasculogenic effect to primary RPE model and produce engineered vessels with similar size and density. FIG. 14I shows VEGF secretion in conditioned media collected from RPE chamber.

FIG. 15A shows retinal pigment epithelium in AMD patients with compromised barrier function and increased drusen deposits on the basolateral side of the RPEs. FIG. 15B shows differentiation of RPEs from both healthy and AMD patient iPSCs. FIG. 15C shows AMD and normal hiPSC-RPEs stained for f-actin, and the RPE markers OTX2, CRALBP, and MCT1. FIGS. 15D-15E show pigmentation of cells in culture of AMD iPS-RPEs for 21 days on BRB chip. FIG. 15F shows decreased expression of RPE-specific marker (RPE65) in the BRB chip. FIG. 15G shows laminin deposition on the basolateral side of RPEs. FIG. 15H shows decreased flow rate and increased number and diameter of drusen-like deposits. FIGS. 15I-15J show decreased expression of tight junction (ZO-1) protein and increased rate of diffusion in AMD model. FIG. 15K shows decreased phagocytosis in AMD patient-derived iPSC-RPEs when treated with pHrodo-labeled particles throughout the 21 days of culture. FIG. 15L shows neovascularization of microengineered vessels co-cultured with AMD iPSC-RPEs. FIG. 15M shows levels of angiogenic factors (VEGF and PEDF) secreted from diseased RPEs.

FIG. 16A shows alternative complement pathway in the RPEs. FIG. 16B shows complement activation in iPSC-RPEs by perfusion of cigarette smoke extract (CSE). FIGS. 16C-16E shows level of complement 3 (FIG. 16C), complement core component (MAC, FIG. 16D) and complement inhibitor (CFH, FIG. 16E). FIG. 16G shows complement activation, phagocytic activity in RPEs after CSE.

DETAILED DESCRIPTION

Figures 1A, 1B, 1C:
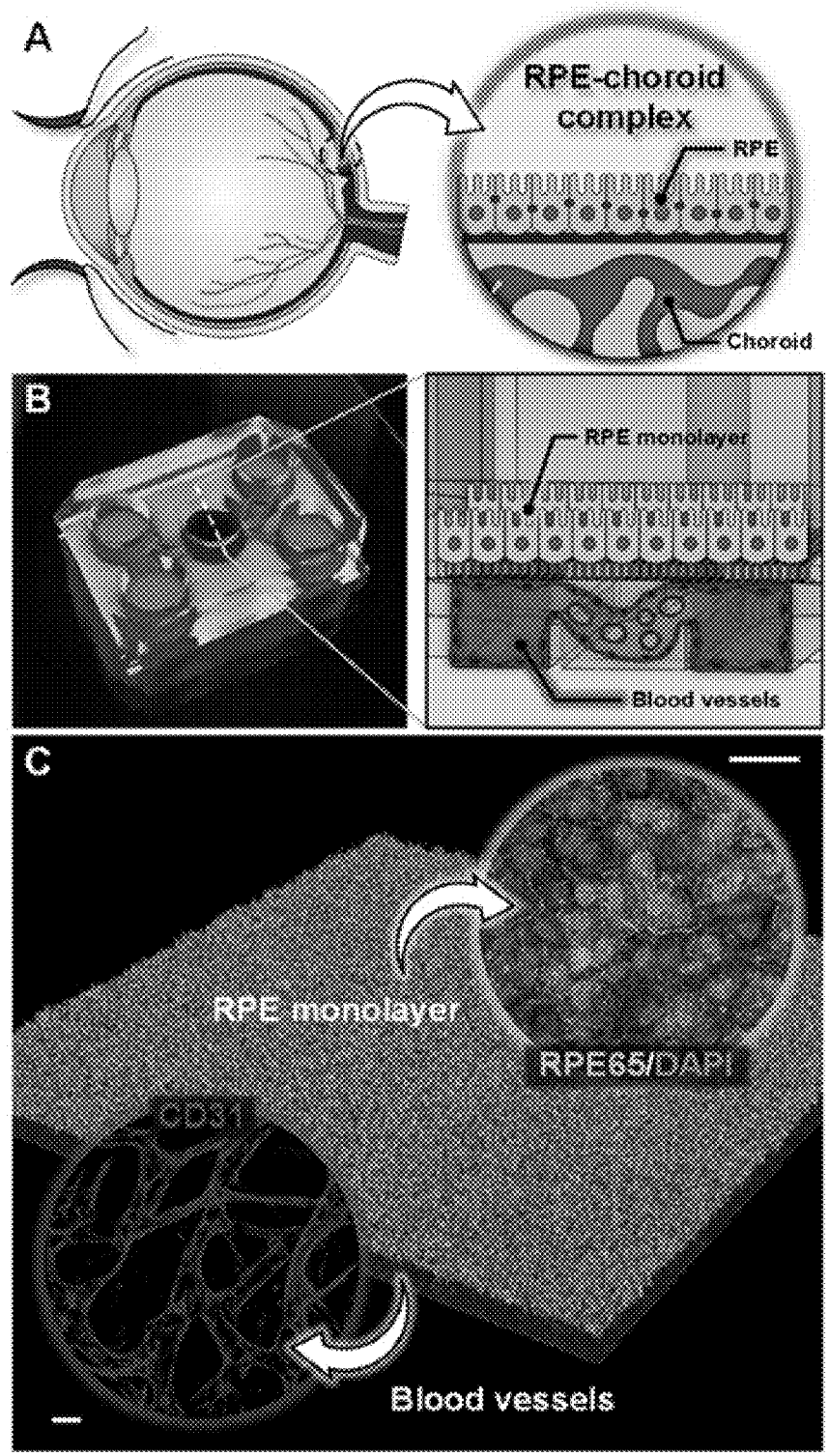
FIGS. 1A-1J illustrate a microengineered model of the human outer blood-retinal barrier (oBRB)-on-a-chip.

The present disclosure provides a microengineered model of the study of the retinal pigment epithelium cells (RPE)-choroid complex in the outer layer of the retina. This bioengineering approach is based on microphysiological culture of primary human retinal cells that mimic this anatomical interface. In certain embodiments, this present disclosure includes induced pluripotent stem cells. Non-limiting embodiments of the present disclosure are described by the present description and examples. For purposes of clarity of disclosure and not by way of limitation, the detailed description is divided into the following subsections:

1. Definitions
2. Organoids-on-chip
3. Methods
4. Kits

1. Definitions

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, more up to 5%, and up to 1% of a given value. Alternatively, particularly with respect to biological systems or processes, the term can mean within an order of magnitude, within 5-fold, and within 2-fold, of a value.

As used herein, the term "biomarker" refers to a marker (e.g., an expressed gene, including mRNA, cellular distribution, histological, and/or protein) that allows detection of a disease in an individual, including detection of disease in its early stages. Biomarkers, as used herein, include histology markers, nucleic acid, and/or protein markers or combinations thereof. In certain non-limiting embodiments, the expression level of a biomarker as determined by mRNA and/or protein levels in an organoid described herein including cells from a subject. In certain non-limiting embodiments, the presence or absence of a biomarker as determined by mRNA and/or protein levels in a biological sample from an individual to be tested is compared with the respective presence or absence in a biological sample from the same individual, another healthy individual, or from the transplanted tissue or organ. In certain non-limiting embodiments, the presence or absence of a biomarker in a biological sample of a subject is compared to a reference control.

As used herein, the term "microfluidic chip" refers to a set of micro-channels etched or molded into a material (e.g., glass, silicon, or polymer such as PDMS). The micro-channels forming the microfluidic chip are connected to achieve the desired features (e.g., mix, pump, sort, or control the biochemical environment). This network of micro-channels trapped into the microfluidic chip is connected to the outside by inputs and outputs pierced through the chip, as an interface between the macro- and micro-world. In certain embodiments, the microfluidic chip is made of PDMS. In certain embodiments, the microfluidic chip is obtained by soft lithography. These options are easy to use and allow a fast process.

As used herein, "retinal pigment epithelial cells" or "RPE cells" refer to cells of the retinal pigment epithelium. This epithelium is a monolayer of pigmented cells situated between the neuroretina and the choroids. The RPE is of neuroectodermal origin and is therefore considered to be part of the retina. The apical membrane of the RPE faces the photoreceptor's outer segments and its basolateral membrane faces Bruch's membrane, which separates the RPE from the fenestrated endothelium of the choriocapillaris. The RPE constitutes the "outer blood-retinal barrier" (BRB or oBRB). The inner BRB is mainly constituted by endothelial cells. Tight junctions between neighboring RPE cells and neighboring endothelial cells are essential in the strict control of fluids and solutes that cross the BRB as well as in preventing the entrance of toxic molecules and plasma components into the retina.

As used herein, the terms "induced pluripotent stem cells" or "iPSCs" or "iPS" refer to cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, and Klf4, Nanog, and Lin28. In certain embodiments, somatic cells are reprogrammed by expressing at least two reprogramming factors, at least three reprogramming factors, or four reprogramming factors to reprogram a somatic cell to a pluripotent stem cell.

As used herein, the terms "age-related macular degeneration" or "AMD" or "ARMD" refer to an eye disease with its onset usually after age 60 that can progressively destroy the macula, the central portion of the retina, impairing central vision. Age-related macular degeneration rarely causes blindness because only the center of vision is affected. However, injury to the macula in the center of the retina can impair the ability to see straight ahead clearly and make it difficult to read, drive, or perform other daily activities that require fine central vision. The macula is in the center of the retina at the back of the eye. During activities such as reading, the light is focused onto the macula where millions of cells change the light into nerve signals that travel to the brain and tell it what the patient is seeing (central vision). With normal central vision, the ability to read, drive, and perform other activities that require fine, sharp, straight-ahead vision is kept. There are two types of AMD: the dry type and the wet type. Neither type causes pain. An early symptom of wet AMD could be that straight lines appear wavy. This happens because blood vessels leak fluid under the macula. The fluid raises the macula from its normal place at the back of the eye and distorts vision. Another sign that a subject may have wet AMD is the rapid loss of central vision. This is different from dry AMD in which loss of central vision occurs slowly. An advanced form of age-related, dry macular degeneration called geographic atrophy leads to progressive and irreversible loss of visual function. Geographic atrophy causes sharply demarcated atrophic lesions of the outer retina, resulting from loss of photoreceptors, retinal pigment epithelium, and choriocapillaris. Geographic atrophy is also known as atrophic age-related macular degeneration. In both dry and wet AMD, the subject may also notice a blind spot. As used herein, the term "biological sample" refers to a sample of biological material obtained from a subject, e.g., a human subject, including a biological fluid, e.g., stem cells, retinal cells, iPSC, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, bronchoalveolar fluid, biliary fluid and combinations thereof. In certain non-limiting embodiments, the presently disclosed subject matter can include iPSC obtained from a biological sample from a subject.

The term "patient" or "subject," as used interchangeably herein, refers to any warm-blooded animal, e.g., a human. Non-limiting examples of non-human subjects include non-human primates, dogs, cats, mice, rats, guinea pigs, rabbits, fowl, pigs, horses, cows, goats, sheep, etc.

2. Organoid-On-Chip

The present disclosure provides cells, tissues, organs, organoids, and tissues-on-a-chip, organs-on-a-chip, and organoids-on-chip that can be used as a model of the outer blood-retinal-barrier (BRB). An "organoid" is a miniaturized and simplified version of an organ produced in vitro in three dimensions that shows realistic micro-anatomy. They are derived from one or a few cells from a tissue, embryonic stem cells, or induced pluripotent stem cells, which can self-organize in three-dimensional culture owing to their self-renewal and differentiation capacities. Standard in vitro models and organoids for studying outer blood-retinal barrier or RPE-choroid complex involve the culture of two or three different cell types (e.g., endothelial cells, fibroblasts, and RPEs) on semipermeable supports. However, these commercially available cell culture platforms are greatly limited in their ability to recapitulate complex three-dimensional structures and dynamic biological microenvironments that play an essential role in health and disease.

FIG. 1A shows that the retina is located in the innermost layer of tissue of the human eye and serves as a light-sensitive layer. The outer BRB is formed at the retinal pigment epithelial (RPE) cell layer that regulates the supply of nutrients and solutes from the choroid to the inner retinal space to maintain overall homeostasis of the tissue.

The present disclosure provides a three dimensional (3D) cell culture model or organoid that can model the RPE-choroid complex in a much more realistic manner. The organoid disclosed herein mimics the exact size of the human outer blood-retinal barrier (human macula diameter=5.5~6 mm; human choroid thickness=250~400 μm, the present blood vessel layer thickness=400 μm) and can be used, without any limitation, as a research platform for studying the development and progression of diseases (e.g., age-related macular degeneration (AMD)) as well as for discovering potential drugs for AMD.

In certain embodiments, the organoid includes a microfluidic chip. In certain embodiments, the microfluidic chip includes multiple layers. The term "layer" includes microchannel layers and gel layers. In certain embodiments, the microfluidic chip includes at least two layers, at least three layers, at least four layers, at least five layers. In certain embodiments, the microfluidic chip includes two layers. In certain embodiments, the microfluidic chip includes a porous membrane. In certain embodiments, the microfluidic chip includes a first and second layer and a porous membrane. In certain embodiments, the porous membrane is positioned between the first and second layers. In certain embodiments, the microfluidic chip is molded into glass. In certain embodiments, the microfluidic chip is molded into ceramic. In certain embodiments, the microfluidic chip is molded into silicone. In certain embodiments, the microfluidic chip is molded into polymers. For example, but without any limitation, the polymer of the microfluidic chip can be polyester (PET), polycarbonate (PC), polydimethylsiloxane (PDMS), cyclic olefin copolymers (e.g., ZEONOR® or TOPAS®), or any combination thereof. In certain embodiments, the polymer is PDMS. In certain embodiments, the microfluidic chip is molded into PDMS. In certain embodiments, the microfluidic chip includes PDMS. Polydimethylsiloxane (PDMS) is an elastomeric polymer that has the advantage of creating flexible molds for 3D cultures. Properties such as easy replica molding, ability to seal with hard surfaces, non-toxicity to cells, and biocompatibility make it a suitable material for molding hydrogel scaffolds. PDMS replicas are typically fabricated by casting the pre-cured PDMS solution on rigid, patterned molds or masters. In the formation of PDMS microfluidic devices and PDMS molds for microgel formation, masters are typically made of silicon or glass. Once pre-cured PDMS prepolymer is fully polymerized, it can be peeled off the surface of the master, resulting in an inverse, replica mold that possesses wells in the shapes of the solid master. The PDMS can be easily sterilized with ethanol and/or exposure to ultra-violet (UV) light.

Figures 12A, 12B, 12C:
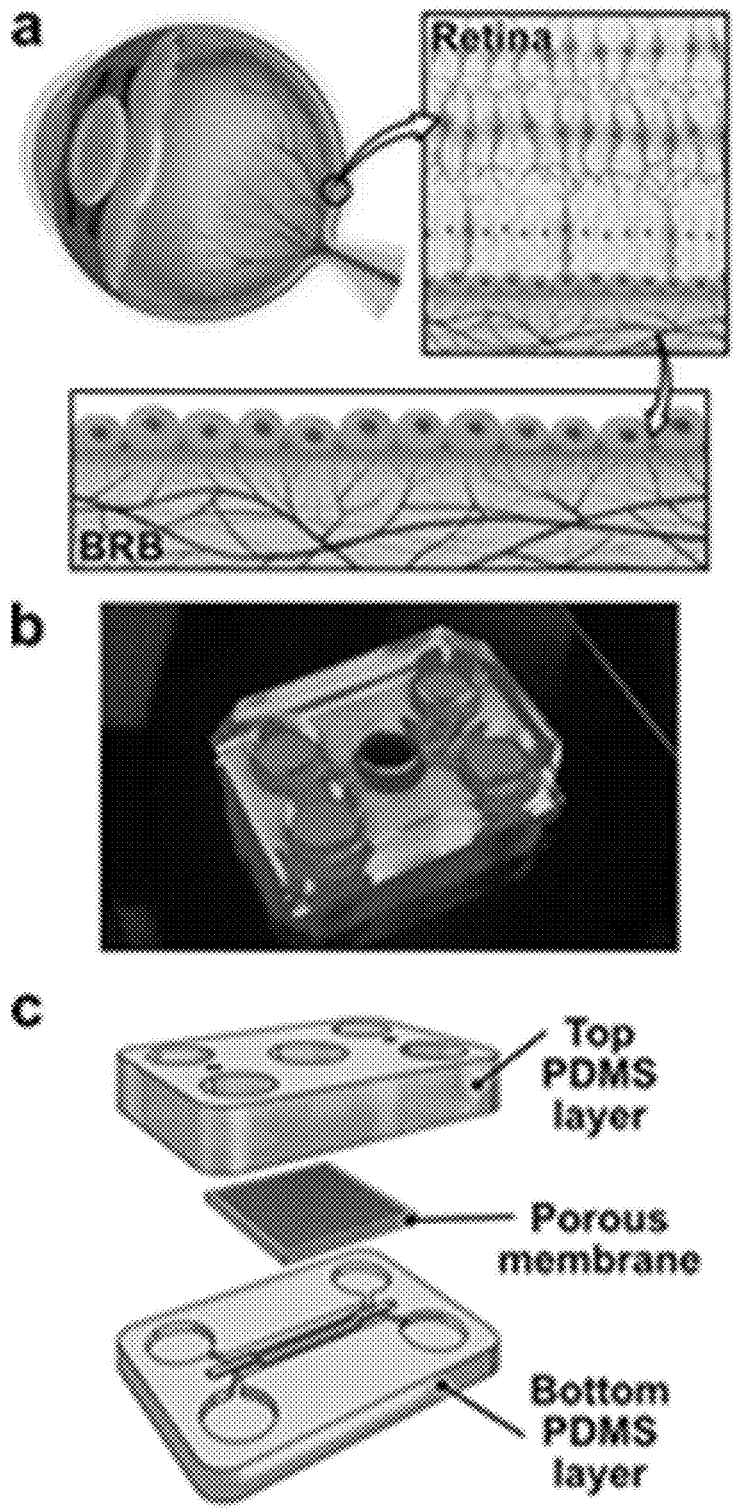
FIGS. 12A-12L illustrate a microengineered model of the human outer blood-retinal barrier (oBRB)-on-a-chip.

An example of microfluidic chip for the present disclosure is depicted in FIG. 1C and FIG. 12C. This representative microfluidic chip consists of two compartments for co-culture of RPEs and perfusable blood vessels. Primary human RPEs were co-cultured in the upper compartment with a network of blood vessels in the lower compartment of the device. To reconstitute the vascular bed of the choroid, an extracellular matrix (ECM) hydrogel scaffold containing human vascular endothelial cells and fibroblasts was created in the lower compartment of the device to induce self-assembly of endothelial cells to 3D vascular networks. In parallel, primary human RPEs were cultured in the upper compartment to form a confluent epithelial monolayer. RPE monolayer and perfusable vessels were confirmed by RPE65 and CD31 immunostaining. In certain embodiments, the top layer provides four cell culture medium reservoirs to the bottom vessel compartment and the center reservoir (diameter=6 mm) serves as an upper compartment for RPE culture. In certain embodiments, the bottom layer is designed to engineer three-dimensional perfusable vascular network. It includes a center lane with phase-guides to hold extracellular matrix (ECM) hydrogel and two side microfluidic channels.

In certain embodiments, the microfluidic chip allows the analysis of the cells by fluorescence microscopy without interfering autofluorescence.

In certain embodiments, the microfluidic chip has a design that allows the growth of the different types of cells. For example, without any limitation, the microfluidic chip includes at least one reservoir for cell culture media. In certain embodiments, the microfluidic chip has a design described in FIG. 12B-12C. For example, without any limitation, the microfluidic chip includes two layers separated by a porous membrane. The top layer and the bottom layer are made of PDMS. The top layer provides four cell culture medium reservoirs to the bottom vessel compartment and a center reservoir serves as an upper compartment for RPE culture. The bottom PDMS layer is designed to engineer a three-dimensional perfusable vascular network. It consists of a center lane with phase-guides to hold extracellular matrix (ECM) hydrogel and two side microfluidic channels. The center reservoir can have different diameters.

In certain embodiments, the microfluidic chip includes a porous membrane. In certain embodiments, the membrane can have about 0.4 μm to about 10 μm pores. In certain embodiments, the pores have a diameter from about 0.5 μm to about 9 μm, about 0.6 μm to about 8 μm, about 0.7 μm to about 7 μm, about 0.8 μm to about 6 μm, about 0.9 μm to about 5 μm, about 1 μm to about 4 μm, about 1.5 μm to about 3.5 μm, or about 2 μm to about 3 μm. In certain embodiments, the pores can be any suitable size. In certain embodiments, the pores can have varying pore sizes. In certain embodiments, the microfluidic chip does not include a porous membrane.

In certain embodiments, the thickness of the membrane can be about 1 μm to about 1 mm. In certain embodiments, the thickness of the membrane can be about 50 μm to about 950 μm, about 100 μm to about 900 μm, about 150 μm to about 850 μm, about 200 μm to about 800 μm, about 250 μm to about 750 μm, about 300 μm to about 700 μm, about 350 μm to about 650 μm, about 400 μm to about 600 μm, or about 450 μm to about 550 μm. In certain embodiments, the thickness of the membrane can be about 100 nanometers to about 5 μm. In certain embodiments, the thickness of the membrane can be about 200 nanometers to about 4 μm, about 300 nanometers to about 3 μm, about 400 nanometers to about 2 μm, about 500 nanometers to about 1 μm, about 600 nanometers to about 900 nanometers, or about 700 nanometers to about 800 nanometers. In certain embodiments, the thickness of the membrane can be about 5 μm to about 100 μm. In certain embodiments, the thickness of the membrane can be about 10 μm to about 90 μm, about 20 μm to about 80 μm, about 30 μm to about 70 μm, about 40 micros to about 60 μm. In certain embodiments, the thickness of the membrane is at least about 5 μm, at least about 10 at least about 20 μm, at least about 30 μm, at least about 40 μm, at least about 50 μm, at least about 60 μm, at least about 70 μm, at least about 80 at least about 90 μm, or at least about 100 In certain embodiments, the membrane can include porous portions and non-porous portions.

In certain embodiments, the membrane can be a thin clear polyester fiber, a polyester membrane, a polytetrafluoroethylene membrane, an elastomeric (e.g., poly(dimethylsiloxane) (PDMS), polyurethane) membrane, a paper membrane, an extracellular matrix membrane, or a natural membrane. In certain embodiments, the natural membrane may include collagen, laminin, any combination thereof, and or any ECM material that can be acquired. The selection of the pore sizes, materials, and other features of the membrane can be varied based on the design of the organoid, the experimental goals, or other suitable motivations. The dissolving membranes can include water-soluble materials (e.g., alginate and Poly-vinyl alcohol (PVA)).

In certain embodiments, the microfluidic chip includes a reservoir. In certain embodiments, the reservoir has a diameter that mimics anatomical structures (e.g., human macula). In certain embodiments, the diameter is about 1 mm to about 8 mm. For example, but without any limitation, the diameter of the reservoir can be about 1 mm, about 1.5 mm, about 2 mm, about 2.5 mm, about 3 mm, about 3.5 mm, about 4 mm, about 4.5 mm, about 5 mm, about 5.1 mm, about 5.2 mm, about 5.3 mm, about 5.4 mm, about 5.5 mm, about 5.6 mm, about 5.7 mm, about 5.8 mm, about 5.9 mm, about 6 mm, about 6.5 mm, about 7 mm, about 7.5 mm, or about 8 mm. In certain embodiments, the diameter is about 5.5 mm. In certain embodiments, the diameter is about 6 mm.

In certain embodiments, the microfluidic chip of the organoid of the present disclosure can include additional elements, including additional membrane layers, for example, but not limited to, integrated pumps, valves, bubble traps, oxygenators, gas-exchangers, in-line microanalytical functions, and other suitable elements. Such elements can allow for additional control and experimentation using the biomimetic organ model. In certain embodiments, the organoid can include features for automatically performing experiments on the microfluidic chip. For example, in some embodiments, the microfluidic chip can incorporate magnetic materials, exothermic or endothermic materials, light-emitting or absorbing materials, mechanically actuatable materials, electrically actuatable materials, or combinations thereof. In certain embodiments, the organoid can be configured to be coupled with other sensors, detectors, or monitors not disclosed on the organoid. In certain embodiments, the organoid can be configured to be coupled with other bioanalytical platforms and methodologies (e.g., gel electrophoresis, capillary electrophoresis, western blotting, ELISA, mass-spectrometry) not disclosed on the organoid.

Figures 1D, 1E, 1F:
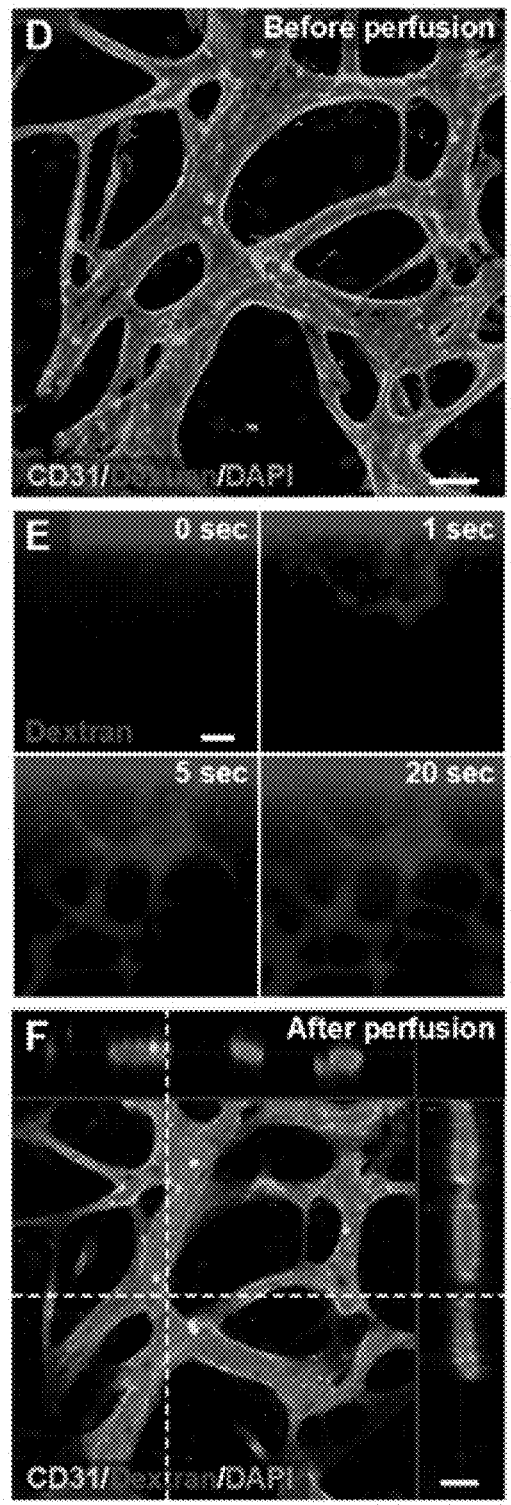

In certain embodiments, the present disclosure provides an organoid including perfusable vessels. As used herein, a "perfusable vessel" refers to a network of cells and additional biocompatible materials that can model and/or mimic the vasculature. For example, a perfusable vessel can act like the endothelium and serve as a permeable barrier for the blood vessel, be involved in the regulation of blood flow, regulate angiogenesis, and/or inflammatory responses. As illustrated in FIGS. 1D-1F, the cells of the perfusable vessels can organize and distribute themselves throughout the scaffold. Further, the perfusability of the vessels can be visualized by the flow of TRITC-dextran in the intravascular space.

In certain embodiments, the perfusable vessel includes endothelial cells. In certain embodiments, the endothelial cells can be primary endothelial cells. In certain embodiments, the endothelial cells can be obtained from a subject. In certain embodiments, the endothelial cells can be derived from stem cells. In certain embodiments, the endothelial cells can be derived from iPSC. In certain embodiments, the endothelial cells can be choroidal endothelial cells. In certain embodiments, the endothelial cells can be immortalized. In certain non-limiting embodiments, for example, the endothelial cells can be Primary Human Umbilical Vein Endothelial Cells (HUVEC). In certain embodiments, the perfusable vessel includes fibroblasts. In certain embodiments, the fibroblasts can be primary fibroblasts. In certain embodiments, the fibroblasts can be obtained from a subject. In certain embodiments, the fibroblasts can be derived from stem cells. In certain embodiments, the fibroblasts can be derived from iPSC. In certain embodiments, the fibroblasts can be choroidal fibroblasts. In certain embodiments, the fibroblasts can be immortalized. In certain non-limiting embodiments, for example, the fibroblasts can be 3T3 embryo fibroblasts.

In certain embodiments, the cells are embedded in an extracellular matrix (ECM) hydrogel scaffold. The extracellular matrix (ECM) is an essential non-cellular component of the tissue microenvironment, included of a network of macromolecules including polysaccharide glycosaminoglycans (GAGs) and proteins such as collagens, laminins, and fibronectin. In addition to providing structural support to cells, ECM can guide cell migration, proliferation, differentiation, and maturation throughout development as well as influence cell function and differentiation in vitro. The presently disclosed subject matter includes scaffolds that include ECM hydrogels to mimic cues within the native microenvironment. As used herein, the term "hydrogel" refers to three dimensional (3D) cross-linked insoluble, hydrophilic networks of polymers that partially resemble the physical characteristics of native ECM. In certain embodiments, the hydrogel includes synthetic polymers or natural polymers. Polymers (synthetic or natural) in hydrogel format can absorb a large amount of water or biological fluid due to the presence of interconnected microscopic pores. In certain non-limiting embodiments, the hydrogel can include polydimethylsiloxane (PDMS), polyamides, poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol) (PEG) hydrogels, poly(methacrylic acid), poly(lactic acid) (PLA), poly(glycolic acid) (PGA), poly(lactide-co-glycolides) (PLGA), polyanhydrides, and polyorthoesters poly(carbonate), poly(acrylo nitrile), poly(ethylene oxide), polyaniline, polyvinyl carbazole, polystyrene and poly(vinyl phenol), polyhydroxyacids, poly(caprolactone), polyanhydrides, polyhydroxyalkanoates, polyurethanes, polysaccharides and poly-biologics such as collagen, albumin, alginate, chitosan, starch, and hyaluronic acid, gelatin, agarose, fibrin, matrigel, glycerol, glycol, and sugar-alcohols, such as mannitol, inositol, xylitol, and adonitol, amino acids such as glycine and arginine, biological polymeric molecules and particularly proteins such as albumin, peptide amphiphiles, and monomers, dimers, and/or oligomers of said materials.

In certain embodiments, the RPE cells can be cultured directly on the surface of the hydrogel without the need for a porous membrane to allow physical contact of RPE cells with the vascular scaffold. For example, by changing the size of the opening of the RPE chamber, hydrogel solution can be injected into the vascular chamber due to surface tension. In certain embodiments, the diameter of this opening is about 500 μm to about 2.5 mm. For example, but without any limitation, if the width of vascular channel is 1 mm, the diameter of the opening is about 500 µm, about 550 µm, about 600 µm, about 650 µm, about 700 µm, about 750 µm, or about 800 µm. If the width of vascular channel is 2 mm, the diameter of the opening is about 1 mm, about 1.1 mm, about 1.2 mm, about 1.3 mm, about 1.4 mm, about 1.5 mm, or about 1.6 mm. If the width of vascular channel is 3 mm, the diameter of the opening is about 2 mm, about 2.1 mm, about 2.2 mm, about 2.3 mm, about 2.4 mm, or about 2.5 mm.

In certain embodiments, the RPE cells can be cultured with other retina cells. In certain embodiments, cells such as photoreceptor cells and/or neural cells and/or glial cells can be cultured on top of the RPE monolayer to mimic the inner retina. In certain embodiments, retina organoids comprise all inner retina cell types can be cultured on top of the RPE monolayer. This allows the BRB chip to replicate complete retina architecture (both inner and outer retina).

In certain embodiments, the perfusable vessels of the organoid have dimensions that mimic physiological and pathophysiological status. In certain embodiments, the perfusable vessels can have a thickness of the human choroid. In certain embodiments, the perfusable vessels can have a thickness of the human choroid during AMD. In certain embodiments, the thickness of the perfusable vessels is about 100 µm to about 600 µm. For example, but without any limitation, the thickness of the perfusable vessels about 100 µm, about 150 µm, about 200 µm, about 250 µm, about 300 µm, about 310 µm, about 320 µm, about 330 µm, about 340 µm, about 350 µm, about 360 µm, about 370 µm, about 380 µm, about 390 µm, about 400 µm, about 410 µm, about 420 µm, about 430 µm, about 440 µm, about 450 µm, about 460 µm, about 470 µm, about 480 µm, about 490 µm, about 500 µm, about 550 µm, or about 600 µm. In certain embodiments, the thickness of the perfusable vessels is about 400 µm.

In certain embodiments, the organoid includes culture media. Culture media can be used to promote and keep differentiation of the RPE or the endothelial cells of the perfusable vessels. In certain embodiments, the culture media includes additional factors to improve the biological functions of the cells in the organoid. For example, but without any limitation, additional factors can include non-essential amino acids, vitamins, 2-mercaptoethanol, growth factors, insulin, FGF1, platelet-poor plasma-derived bovine serum, retinoic acid, basic FGF, noggin, the small molecule TGF-beta inhibitor SB431542, Activin A, BMP-4, Wnt, epidermal growth factor (EGF), ascorbic acid, retinoic acid, heparin, hydrocortisone, gentamicin, fetal bovine serum, Insulin-like growth factor (IGF), and vascular endothelial growth factor (VEGF).

3. Methods

In certain embodiments, the present disclosure provides methods of fabricating the organoid. In certain embodiments, the methods can include fabricating a microfluidic chip described herein. The microfluidic chip can be built by any methods known in the art, including, but not limited to, those outlined in Huh et al., Nature Protocols 8:2135-2157 (2013).

For example, without any limitation, FIG. 12C provides an embodiment of these methods. In the certain embodiments, the methods of fabricating include encapsulating endothelial cells and fibroblasts in ECM hydrogel, injecting the cells into the center lane of the bottom PDMS layer, seeding endothelial cells in two side lumens to form entotheliazed channels for anastomosis, seeding RPEs on the top center reservoir, culturing the organoid to allow RPEs to form tight junctions and make the barrier and to allow endothelial cells and fibroblasts to form perfusable vessels.

In certain embodiments, the components of the microfluidic chip can include chemical binding, i.e., oxygen plasma treatment of PDMS. Chemical binding can result in cell death; therefore, if the microfluidic chip is chemically bonded together, the cells can be added to the microfluidic chip after chemical binding is complete. In certain embodiments, the components of the microfluidic chip can include mechanical binding. Mechanical binding allows the different components to be cultured separately before interfacing them together. In certain embodiments, mechanical binding of the layers includes a clamp A clamp includes, but is not limited to a screw clamp, cam clamp, spring clamp, binder clip, vice, C-clamp, adjustable hand screw clamp, spring clamp, pipe clamp, bar clamp, parallel clamp, F style clamp, or a threaded rod with one or more fasteners. In certain embodiments, the method can include binding the components of the microfluidic chip using adhesive materials. Adhesive materials include, but are not limited to, double-sided tape, hemming tape, removable adhesive fabric, rubber cement, adhesive polymers (e.g., polysulfones, polyethersulfones, polyimides, polyamide-imides, epoxy resins, polyarylene ether ketones such as, chloromethylated polyarylene ether ketones, acryloylated polyarylene ether ketones, and mixtures thereof, preformed polyimides, polyetherimides, polystyrene, and the like and cholromethylated polyethersulfones and acryloylated polyethersulfones). In certain embodiments, the method can include bonding components of the microfluidic chip using negative pressure (e.g., vacuum).

In certain embodiments, the different components of the microfluidic chip can be combined in modular fashion according to a desired time sequence. In certain embodiments, the entire microfluidic chip does not need to assemble at first. In certain embodiments, the method can include casting a gel in the chamber of the chamber slab. In certain embodiments, the method can include casting a gel to attach to a membrane.

Gel casting can involve any standard method known to one of skill in the art. In certain embodiments, techniques are used to induce surface modification to promote collagen/ ECM anchoring. In certain embodiments, the casting of a gel can include sulfo-sanpah treatment of the chamber slab material to promote collagen/ECM anchorage. In certain embodiments, the casting of a gel can include sulfo-sanpah treatment of the membrane material and channel material to promote collagen/ECM anchorage. For example, the surface of the portion of the chamber slab in which the gel layer can be attached to can be treated with sulfo-sanpah and exposed to UV light (for example two times at 5 minutes each). In certain embodiments, the gel is prepared with cells and pipetted onto the chamber. The density of the cells can range from about $1\times10^4$ cells to $1\times10^8$, depending on the experiment and the culture condition of the cells. One of ordinary skill would understand the cell density and culture conditions required for each particular gel layer. In certain embodiments, the gel is prepared without cells and pipetted onto the chamber or a membrane. If the microfluidic chip is already bound together, the cells can be placed into one of the channels and transmigrate to populate the empty gel.

In certain embodiments, the organoid (e.g., microfluidic chip including the cell described herein) can be cultured for a time necessary for cell differentiation and development. In certain embodiments, the culturing of the cells in the organoid occurs of a period of about 2 days, about 3 days, about 4 days, about 5 days, about 6 days, about 7 days, about 8 days, about 9 days about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, or about 25 days.

In certain embodiments, a device can deliver culture medium to the microfluidic chip of the organoid. In certain embodiments, the device can pump culture medium to the microfluidic chip through a port, wherein the port can be to the outside of the microfluidic chip. In certain embodiments, the device can pump culture medium to the microfluidic chip through a port, wherein the port can be to the inside of the microfluidic chip. In certain embodiments, cell culture media with different constituents can be added to separate ports of the microfluidic chip.

In certain embodiments, the pharmacological properties of different compounds can be tested using the three dimensional in vitro organoid disclosed herein. In certain embodiments, the present disclosure provides methods for using the organoid disclosed herein. In certain embodiments, the methods include preparing a three dimensional in vitro organoid disclosed herein. Additional details of the organoid are described in Section 2. In certain embodiments, the methods include obtaining retinal pigment epithelial cells from a subject. In certain embodiments, the methods include preparing the organoid using retinal pigment epithelial cells from a subject. In certain embodiments, the methods include contacting a test agent with the organoid. As used herein, a "test agent" is any chemical, which, in a solution of sufficient concentration, can modify a biological response or a biomarker of cells or tissues exposed to the solution. For example, a test agent can modify the expression of one of more proteins in endothelial cells present in the organoid. In certain embodiments, a test agent is capable of increasing a biomarker. In certain embodiments, a test agent is capable of reducing a biomarker. In certain embodiments, a test agent is capable of inducing a temporary modulation of the biomarker. In certain embodiments, a test agent is capable of inducing a non-reservable modulation of the biomarker. In certain non-limiting embodiments, for example, the biomarkers can include C-reactive protein, cytokines, tissue necrosis factor alpha receptor-II (TNF-R2), cellular adhesion molecules, IL1, IL2, IL3, IL4, IL5, IL6, IL7, IL8, IL9, IL10, IL11, IL12, IL13, IL14, IL15, IL16, IL17, integrins, intracellular adhesion molecules (e.g., ICAM-1, ICAM-3), B-lymphocyte cell adhesion molecule (BL-CAM), lymphocyte function-associated adhesion molecules (e.g., LFA-2), vascular cell adhesion molecules (e.g., VCAM-1), neural cell adhesion molecule (NCAM), platelet endothelial cell adhesion molecule (PECAM), and soluble intercellular adhesion molecule (sICAM-1), intracellular adhesion molecule (ICAM), vascular adhesion molecule (VCAM), homocysteine (HCY), apolipoprotein B (ApoB) or lipoprotein A (LP(a)). In certain non-limiting embodiments, for example, the biomarker can include RPE65 expression, hypopigmentation, number of drusen-like basal deposits, size of drusen-like basal deposit, laminin expression, collagen expression, phagocytic activity, caspase activity, apoptotic activity, secretion of cytokines, secretion of complement proteins, or any combination thereof. In certain embodiments, the secretion of cytokines includes secretion of pigment epithelium-derived factor (PEDF). In certain embodiments, the secretion of cytokines includes secretion of vascular endothelium growth factor (VEGF). In certain embodiments, the secretion of complement proteins includes secretion of C3, CFH, CFI, CD46, CD59, CD5b-9, or any combination thereof. In certain embodiments, a level of a biomarker in an organoid can be obtained by any art recognized method. For example, without any limitation, the level can be determined by histological analysis, PCR, qPCR, sequencing, NGS, immunofluorescence, annexin V assay, caspase activity assays, enzyme-linked immunoassays (EIA), or other known techniques for determining the presence and/or quantity of the marker.

Figures 1G, 1H, 1I, 1J:
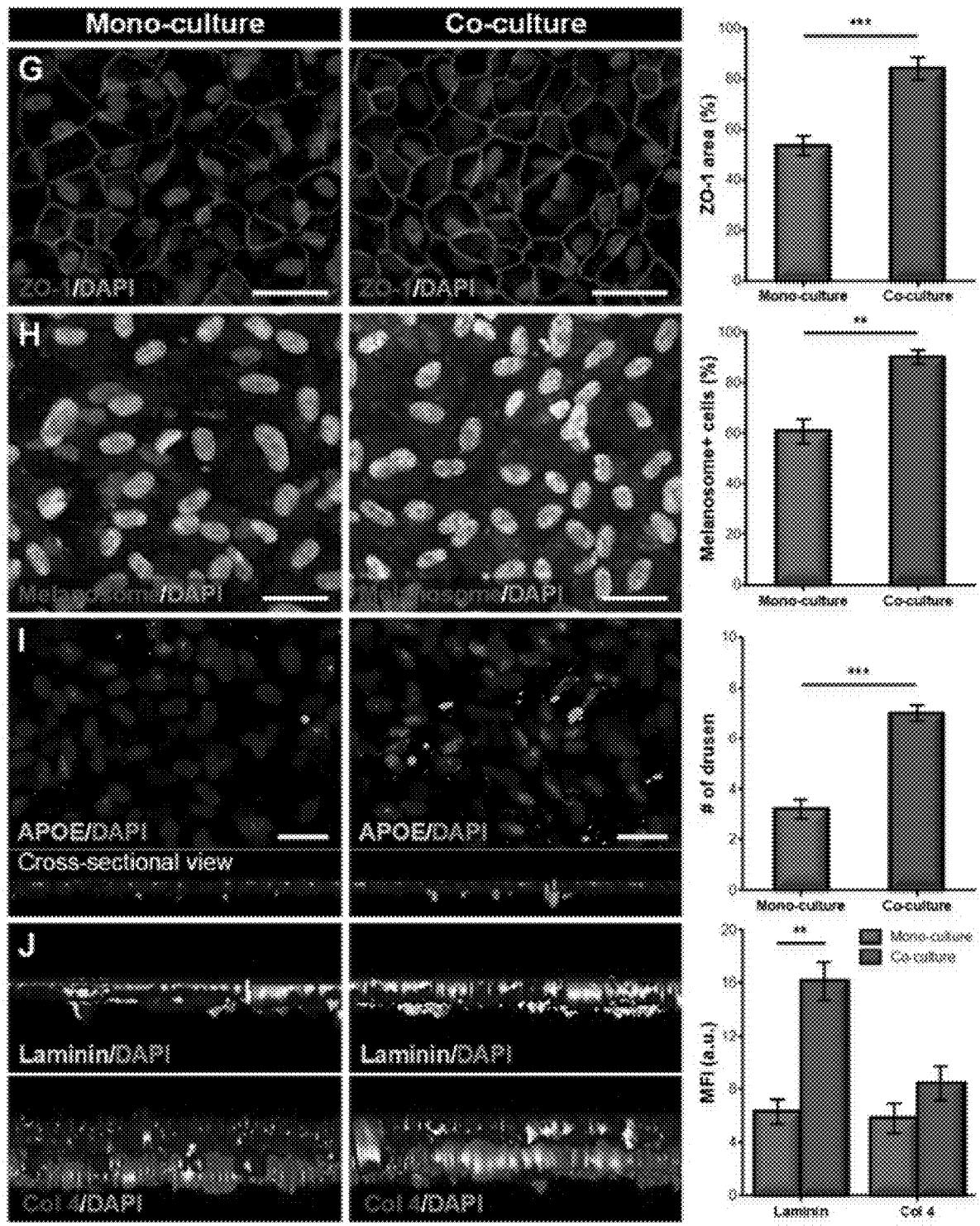
Figure 2:
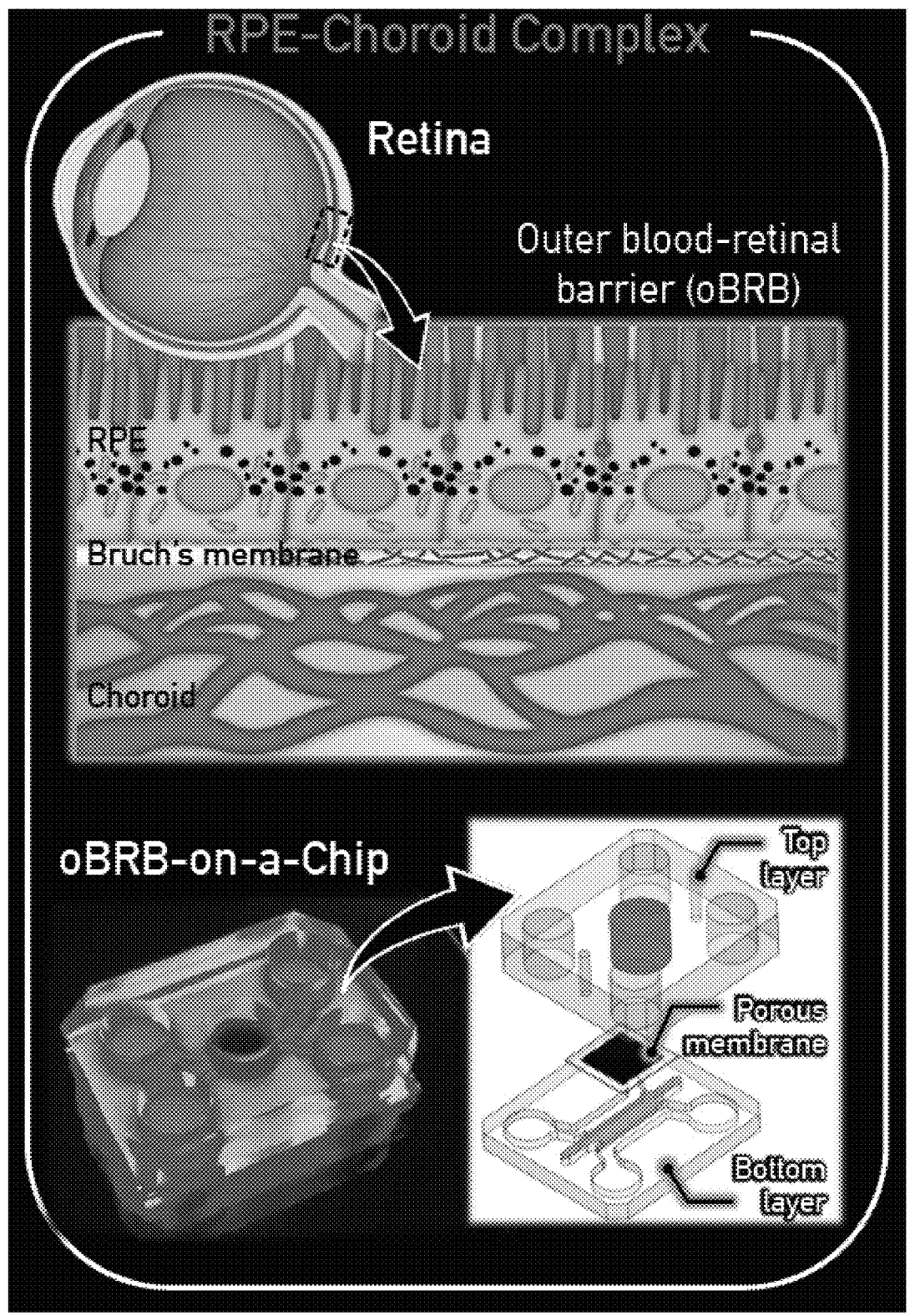
FIG. 2 illustrates a retinal pigment epithelium (RPE)-choroid complex in the outer layer of the retina and a diagram of the oBRB-on-a-chip model.
Figure 3:
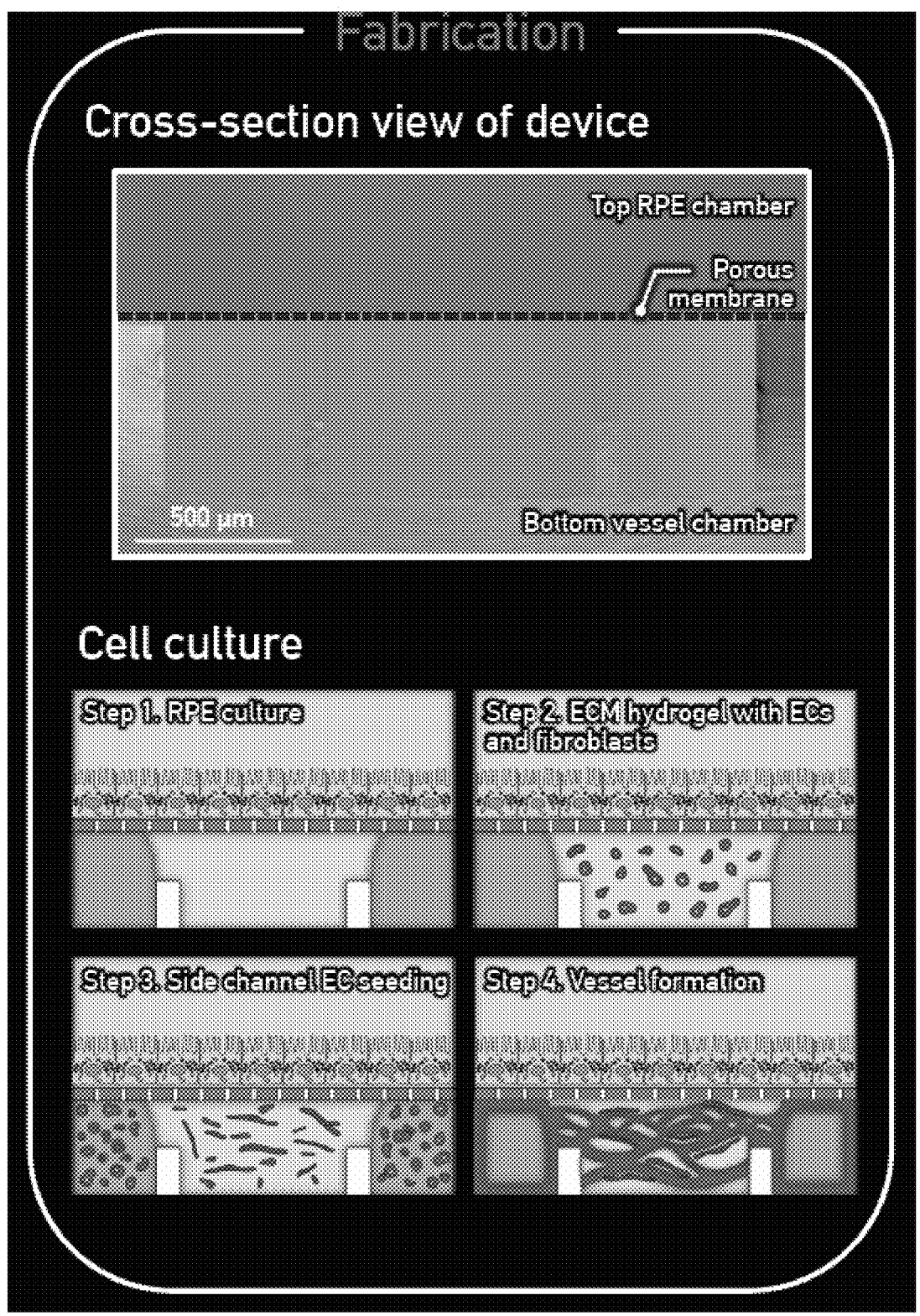
FIG. 3 illustrates methods of fabrication of the device.
Figure 4:
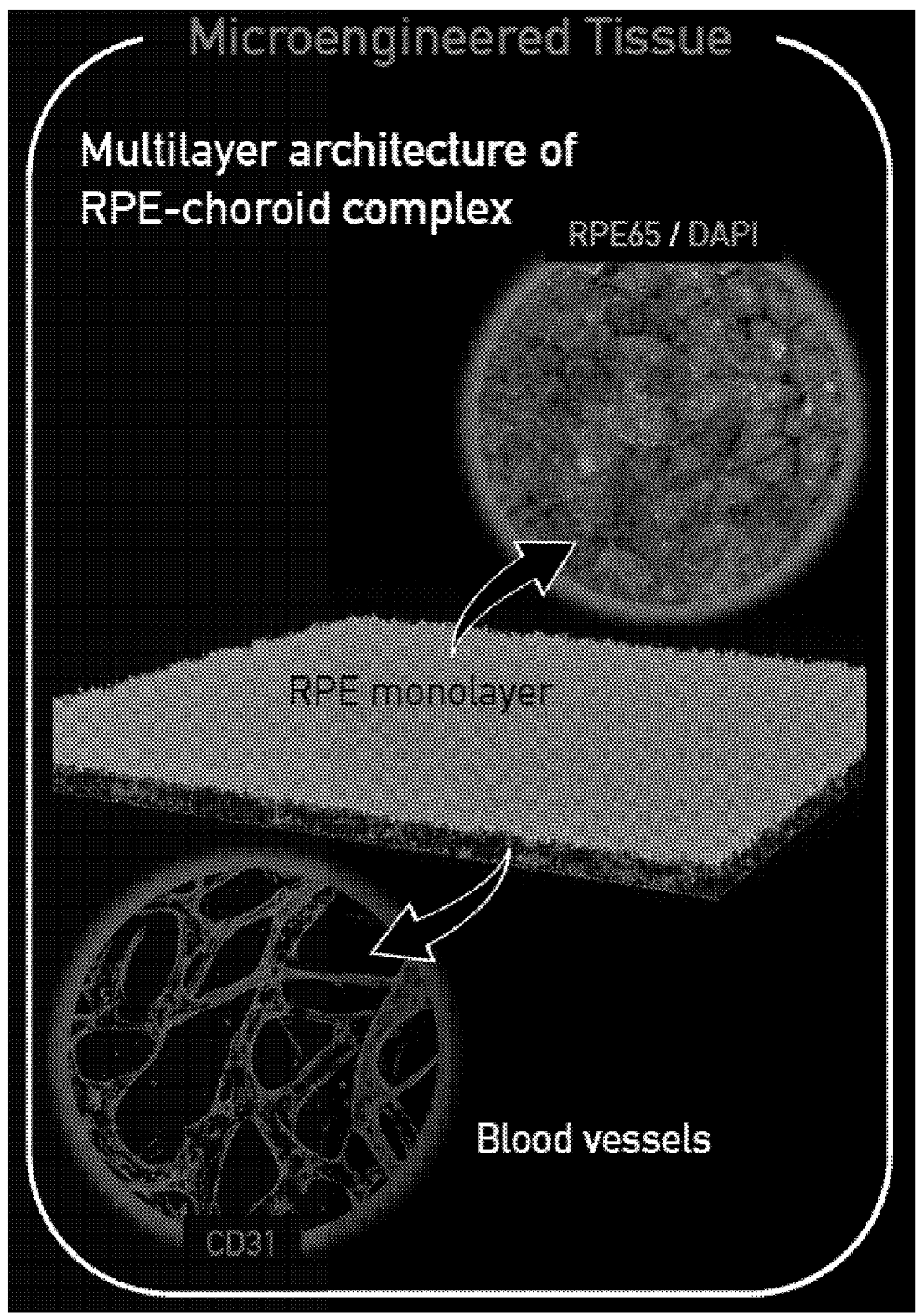
FIG. 4 illustrated the multilayer architecture of the RPE-choroid complex.
Figure 5:
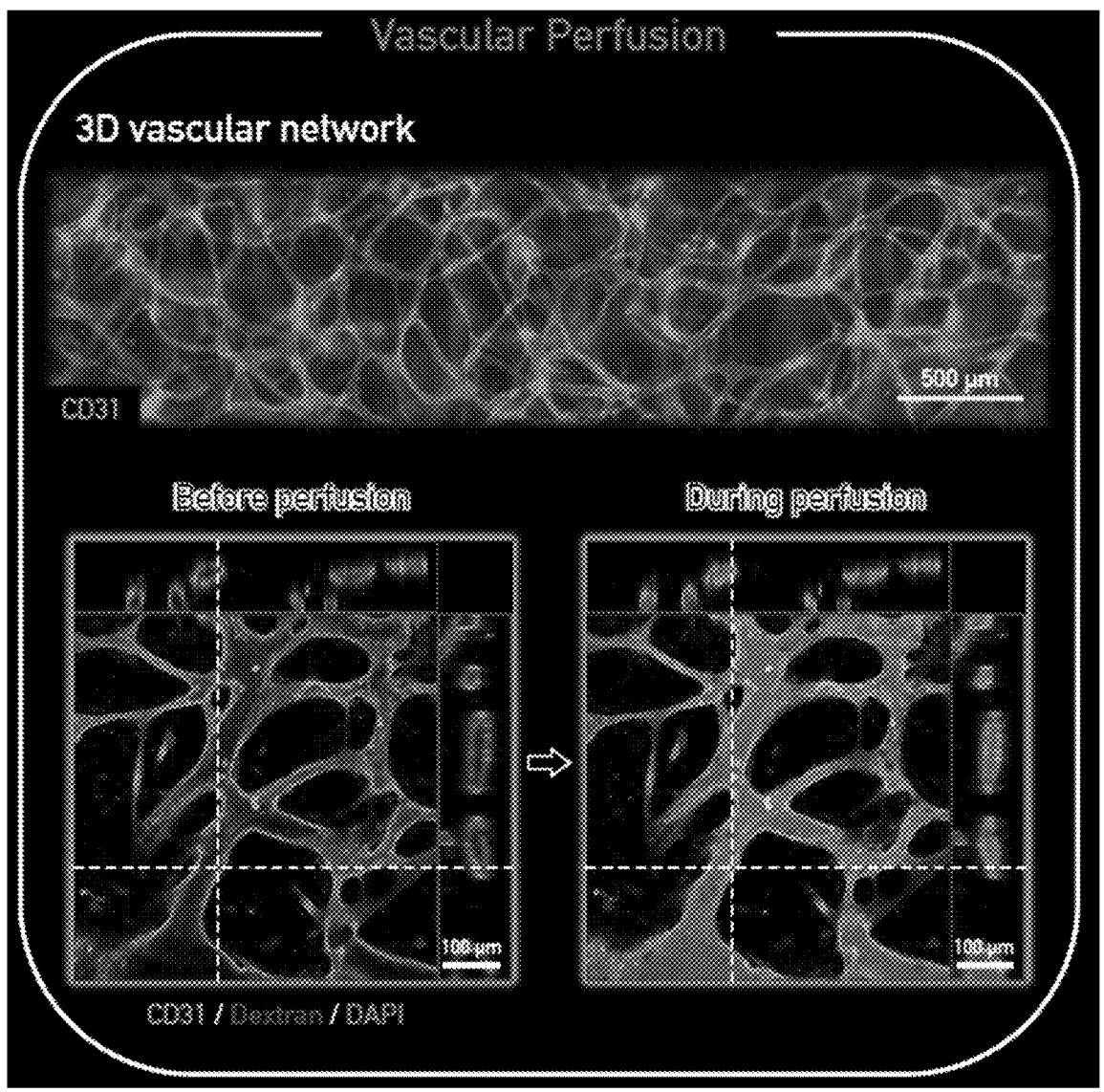
FIG. 5 illustrates the vascular perfusion in the device.

In certain embodiments, the biomarker can include the expression of ZO-1. For example, without any limitation, FIG. 1G shows that after 21 days of culture, the epithelial barrier of the organoid formed well defined tight junction as evidenced by robust expression of ZO-1. Additional examples of biomarkers can include RPE pigmentation, production of basal deposits and basement membrane proteins. As illustrated in FIGS. 1G-1J, the biomarkers included tight junction (ZO01) formation, pigmentation (melanosome), drusen generation (APOE), and basement membrane protein productions (laminin and Col 4) in RPE monoculture and RPE-choroid co-culture models. These biomarkers were visualized by immunostaining.

In certain embodiments, the biomarker can include complement proteins. Complement activation in the retina is an important indicator of chronic inflammation and may contribute to pathology in AMD disease states. As shown in Example Section, to mimic early stage of inflammation, control iPS-RPEs were exposed to low (1%) and high (5%) concentration of cigarette smoke extracts (CSE) and complement proteins were analyzed in CSE groups and dry AMD group. Both control-CS5% and AMD groups showed similar CFH and C5b-9 levels along with similar trends of complement protein secretion in cell culture supernatant which was measured by ELISA. Using the oBRB-on-a-chip disclosed herein, complement inhibitory drug can be tested to find a potential dry AMD drug that can suppress chronic inflammation.

In certain embodiments, the biomarker can include phagocytic activity. In the human retina, RPEs constantly phagocytose shedded photoreceptor outer segment membranes to clear out the fragments. Phagocytic function of the RPE can be measured using pHrodo which increases fluorescence once they are ingested.

Methods for the detection of protein biomarkers are well known to those skilled in the art, and include but are not limited to mass spectrometry techniques, 1-D or 2-D gel-based analysis systems, chromatography, enzyme linked immunosorbent assays (ELISAs), radioimmunoassays (MA), enzyme immunoassays (EIA), Western Blotting, immunoprecipitation and immunohistochemistry. These methods use antibodies, or antibody equivalents, to detect protein, or use biophysical techniques. Antibody arrays or protein chips can also be employed, see for example U.S. Patent Application Nos: 2003/0013208A1 2002/0155493A1, 2003/0017515 and U.S. Pat. Nos. 6,329,209 and 6,365,418, herein incorporated by reference in their entireties. ELISA and RIA procedures can be conducted such that a biomarker standard is labeled (with a radioisotope, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker in the sample is allowed to react with the corresponding immobilized antibody, radioisotope or enzyme-labeled anti-biomarker antibody is allowed to react with the system, and radioactivity or the enzyme assayed (ELISA-sandwich assay). Other conventional methods can also be employed as suitable. The above techniques can be conducted essentially as a "one-step" or "two-step" assay. A "one-step" assay involves contacting antigen with immobilized antibody and, without washing, contacting the mixture with labeled antibody. A "two-step" assay involves washing before contacting the mixture with labeled antibody. Other conventional methods can also be employed as suitable.

In certain embodiments, a method for measuring biomarker expression includes contacting a biological sample, e.g., a fragment of the organoid, with an antibody or variant thereof which selectively binds the biomarker, and detecting whether the antibody or variant thereof is bound to the sample. A method can further include contacting the sample with a second antibody, e.g., a labeled antibody. The method can further include washing, e.g., to remove one or more reagents.

Other techniques can be used to detect a biomarker according to a practitioner's preference based upon the present disclosure. One such technique that can be used for detecting and quantitating biomarker protein levels is Western blotting (Towbin et al., Proc. Nat. Acad. Sci. 76:4350 (1979)). Organoids and/or cells can be frozen, homogenized in lysis buffer, and the lysates subjected to SDS-PAGE and blotting to a membrane, such as a nitrocellulose filter. Antibodies (unlabeled) are then brought into contact with the membrane and assayed by a secondary immunological reagent, such as labeled protein A or anti-immunoglobulin (suitable labels including horseradish peroxidase and alkaline phosphatase). Chromatographic detection can also be used. In certain embodiments, immunodetection can be performed with an antibody to a biomarker using the enhanced chemiluminescence system (e.g., from PerkinElmer Life Sciences, Boston, Mass.). The membrane can then be stripped and re-blotted with a control antibody, e.g., anti-actin (A-2066) polyclonal antibody from Sigma (St. Louis, Mo.).

Immunohistochemistry can be used to detect the expression and/or presence of a biomarker, e.g., in a biopsy sample. A suitable antibody is brought into contact with, for example, a layer of cells in the organoid, followed by washing to remove unbound antibody, and then contacted with a second, labeled, antibody. Labeling can be by fluorescent markers, enzymes, such as peroxidase, avidin, or radiolabeling. The assay is scored visually, using microscopy and the results can be quantitated.

Other machine or autoimaging systems can also be used to measure immunostaining results for the biomarker. As used herein, "quantitative" immunohistochemistry refers to an automated method of scanning and scoring samples that have undergone immunohistochemistry, to identify and quantitate the presence of a specified biomarker, such as an antigen or other protein. The score given to the sample is a numerical representation of the intensity of the immunohistochemical staining of the sample, and represents the amount of target biomarker present in the sample. As used herein, Optical Density (OD) is a numerical score that represents intensity of staining. As used herein, semi-quantitative immunohistochemistry refers to scoring of immunohistochemical results by human eye, where a trained operator ranks results numerically (e.g., as 1, 2 or 3).

Various automated sample processing, scanning and analysis systems suitable for use with immunohistochemistry are available in the art. Such systems can include automated staining (see, e.g., the Benchmark system, Ventana Medical Systems, Inc.) and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immune-stained samples. See, e.g., the CAS-200 system (Becton, Dickinson & Co.). Antibodies against biomarkers can also be used for imaging purposes, for example, to detect the presence of a biomarker in cells of a subject. Suitable labels include radioisotopes, iodine ($^{125}$I, $^{121}$I) carbon (14C), sulphur ($^{35}$S), tritium ($^{3}$H), indium ($^{112}$In), and technetium, fluorescent labels, such as fluorescein and rhodamine and biotin. Immunoenzymatic interactions can be visualized using different enzymes such as peroxidase, alkaline phosphatase, or different chromogens such as DAB, AEC, or Fast Red.

In addition, a biomarker can be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See, for example, U.S. Patent Application Nos: 20030199001, 20030134304, 20030077616, which are herein incorporated by reference. Mass spectrometry methods are well known in the art and have been used to quantify and/or identify biomolecules, such as proteins (see, e.g., Li et al. (2000) Tibtech 18: 151-160; Rowley et al. (2000) Methods 20: 383-397; and Kuster and Mann (1998) Curr. Opin. Structural Biol 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modem laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI can have limitations as an analytical tool for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait).

For additional information regarding mass spectrometers, see, e.g., Principles of Instrumental Analysis, 3rd edition. Skoog, Saunders College Publishing, Philadelphia, 1985; and Kirk-Othmer Encyclopedia of Chemical Technology, 4th ed. Vol. 15 (John Wiley & Sons, New York 1995), pp. 1071-1094. Any method for qualitatively or quantitatively detecting a nucleic acid biomarker can be used. Detection of RNA transcripts can be achieved, for example, by Northern blotting, wherein a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography. Detection of RNA transcripts can further be accomplished using amplification methods. For example, it is within the scope of the present disclosure to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). In certain embodiments, quantitative real-time polymerase chain reaction (qRT-PCR) is used to evaluate mRNA levels of biomarker. In certain embodiments, the levels of one or more biomarkers can be quantitated in a biological sample.

In situ hybridization visualization can also be employed, wherein a radioactively labeled antisense RNA probe is hybridized with a thin section of a biopsy sample, washed, cleaved with RNase and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used. Another method for evaluation of biomarker expression is to detect mRNA levels of a biomarker by fluorescent in situ hybridization (FISH). FISH is a technique that can directly identify a specific region of DNA or RNA in a cell and therefore enables to visual determination of the biomarker expression in tissue samples. The FISH method can have the advantages of a more objective scoring system and the presence of a built-in internal control consisting of the biomarker gene signals present in all non-neoplastic cells in the same sample. Fluorescence in situ hybridization is a direct in situ technique that is relatively rapid and sensitive. FISH test also can be automated. Immunohistochemistry can be combined with a FISH method when the expression level of the biomarker is difficult to determine by immunohistochemistry alone.

Alternatively, mRNA expression can be detected on a DNA array, chip or a microarray. Oligonucleotides corresponding to the biomarker(s) are immobilized on a chip which is then hybridized with labeled nucleic acids of a test sample obtained from a subject. Positive hybridization signal is obtained with the sample containing biomarker transcripts. Methods of preparing DNA arrays and their use are well known in the art. (See, for example, U.S. Pat. Nos. 6,618,6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Dmg discovery Today 5: 59-65, which are herein incorporated by reference in their entirety). Serial Analysis of Gene Expression (SAGE) can also be performed (See for example U.S. Patent Application 20030215858). To monitor mRNA levels, for example, mRNA can be extracted from the organoid to be tested, reverse transcribed and fluorescent-labeled cDNA probes are generated. The micro arrays capable of hybridizing to a biomarker, cDNA can then probed with the labeled cDNA probes, the slides scanned and fluorescence intensity measured. This intensity correlates with the hybridization intensity and expression levels. Types of probes for detection of RNA include cDNA, riboprobes, synthetic oligonucleotides and genomic probes. The type of probe used will generally be dictated by the particular situation, such as riboprobes for in situ hybridization, and cDNA for Northern blotting, for example. In certain embodiments, the probe is directed to nucleotide regions unique to the particular biomarker RNA. In certain embodiments, the present disclosure provides methods for examining AMD. In certain embodiments, the methods include using an organoid described herein. In certain embodiments, the methods include culture conditions that affect the functionality of the RPE and/or endothelial cells. The culture conditions influence the behavior of the cells and can vary from conditions.

4. Kits

In certain non-limiting embodiments, the present disclosure provides for a kit for assessing the effects of a test agent on the organoid disclosed herein. Types of kits include, but are not limited to, packaged culture media, growth factors, microfluidic chips, hydrogels, polymers, endothelial cells, fibroblasts, probe and primer sets (e.g., TaqMan probe/primer sets), arrays/microarrays, antibodies, and antibody-conjugated beads, and other reagents for using one or more organoids disclosed herein.

In certain non-limiting embodiments, a kit can include at least one antibody for immunodetection of the biomarker and/or for the isolation of the cells obtained from a subject (e.g., isolation of REP from a subject). Antibodies, both polyclonal and monoclonal, specific for a biomarker, can be prepared using conventional immunization techniques, as will be generally known to those of skill in the art. The immunodetection reagents of the kit can include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels (3H, 35S, 32P, 14C, 131I) or enzymes (alkaline phosphatase, horseradish peroxidase).

In certain non-limiting embodiments, the antibody can be provided bound to a solid support, such as a column matrix, an array, or well of a microtiter plate. Alternatively, the support can be provided as a separate element of the kit.

In certain non-limiting embodiments, a kit can include a pair of oligonucleotide primers suitable for polymerase chain reaction (PCR) or nucleic acid sequencing, for detecting one or more biomarkers. A pair of primers can include nucleotide sequences complementary to a biomarker, and be of sufficient length to selectively hybridize with said biomarker. Alternatively, the complementary nucleotides can selectively hybridize to a specific region in close enough proximity 5' and/or 3' to the marker position to perform PCR and/or sequencing. Multiple marker-specific primers can be included in the kit to simultaneously assay large number of markers. The kit can also include one or more polymerases, reverse transcriptase and nucleotide bases, wherein the nucleotide bases can be further detectably labeled.

In certain non-limiting embodiments, the oligonucleotide primers can be immobilized on a solid surface or support, for example, on a nucleic acid microarray, wherein the position of each oligonucleotide primer bound to the solid surface or support is known and identifiable.

In certain non-limiting embodiments, a kit can include one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction to detect a biomarker. A kit can also include additional components or reagents necessary for the detection of a biomarker, such as secondary antibodies for use in immunohistochemistry.

In certain embodiments, the kit of the present disclosure includes reagents and instruction to prepare the organoid described in Section 2. In certain embodiments, the kit of the present disclosure includes reagents and instruction to perform any of the methods described in Section 3.

The following examples are offered to more fully illustrate the disclosed subject matter, but are not to be construed as limiting the scope thereof.

EXAMPLES

Example 1

Age-related macular degeneration (AMD) is a leading cause of visual impairment and blindness in the people over the age of 60, with more than 200,000 US cases per year. Visual dysfunction in AMD is associated with the degeneration of retinal pigmented epithelium (RPE) cells that begins with impaired clearance of cellular waste material. This leads to a state of chronic inflammation in the eye in addition to the formation of abnormal deposits underneath RPE cells called drusen, which impair the function of RPE cells. Despite great interest in improving the quality of life of AMD patients, there are currently no clinical treatments available for dry AMD, which is the most common form of the disease. Rodent models have been used for AMD studies; however, these models have limitations to fully mimic characteristics of the human AMD as rodents lack macula in the retina. Thus, in order to study the pathophysiology of AMD, innovative human cell-based in vitro models with the ability to recapitulate the RPE-choroid complex in the outer blood-retinal barrier of the retina are required.

Figures 12D, 12E, 12F, 12G, 12H:
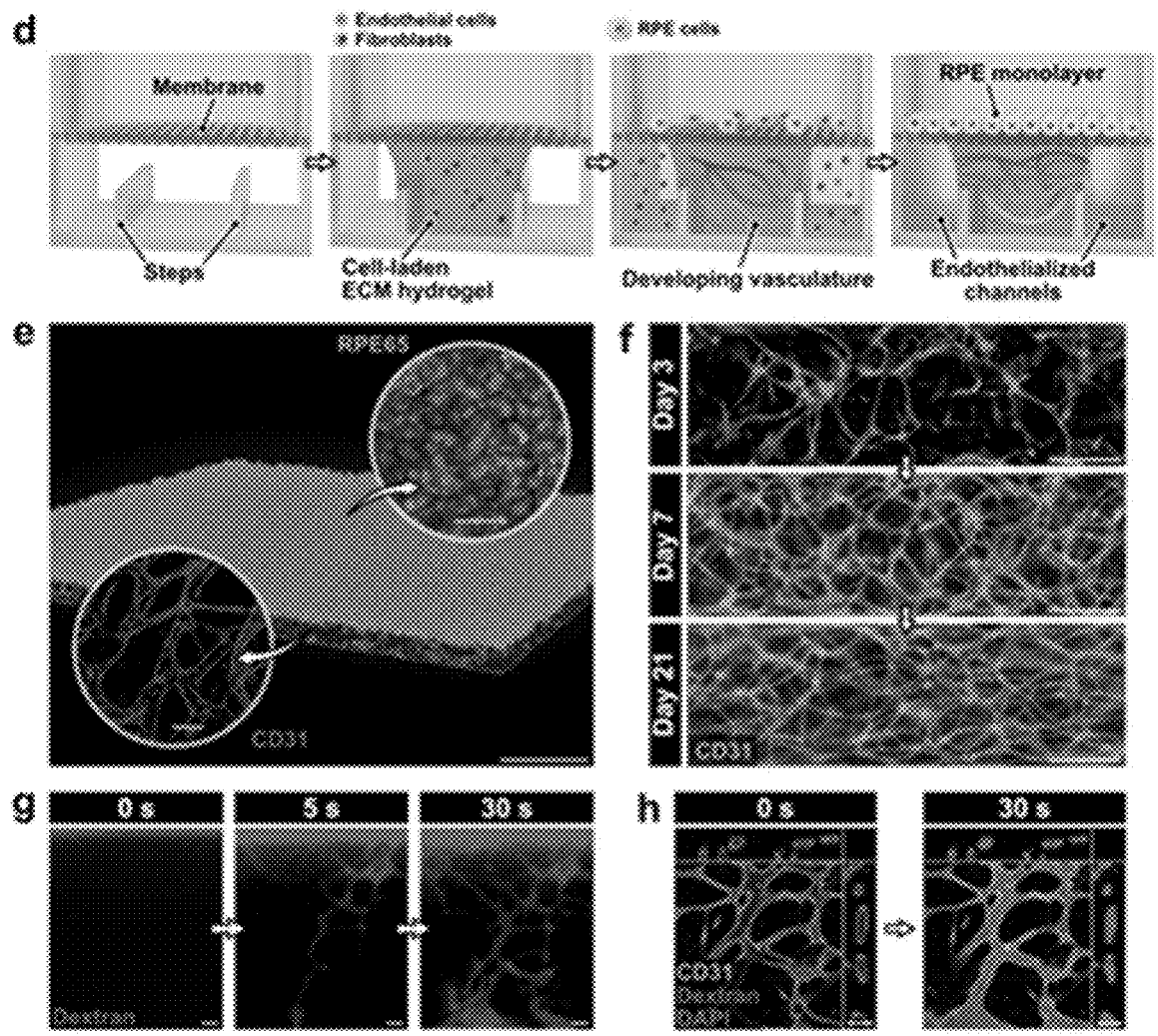

The present example describes a unique bioengineering approach based on microphysiological culture of primary and induced pluripotent stem cell (iPSC)-derived human RPEs to mimic this important tissue-tissue interface during AMD. The presently disclosed microphysiological model was constructed in a PDMS device that consisted of two compartments for co-culture of RPEs and perfusable blood vessels (FIGS. 12B-12C). To reconstitute the vascular bed of the choroid, an extracellular matrix (ECM) hydrogel scaffold containing human vascular endothelial cells and fibroblasts was created in the lower compartment of the device to induce self-assembly of endothelial cells to 3D vascular networks. In parallel, primary human RPEs or iPSC-derived RPEs were cultured in the upper compartment to form a confluent epithelial monolayer. The endothelial cells embedded in the ECM hydrogel organized themselves into perfusable blood vessels distributed throughout the scaffold (FIG. 12D). After 21 days of culture, the epithelial barrier formed well-defined tight junctions as evidenced by robust expression of zonula occludens-1 (ZO-1). Importantly, this characterization revealed that the engineered vessels induced vessels induced significant increase in the expression of ZO-1, RPE pigmentation and the production of basal deposits and basement membrane proteins (FIGS. 12E-12G).

Figure 6:
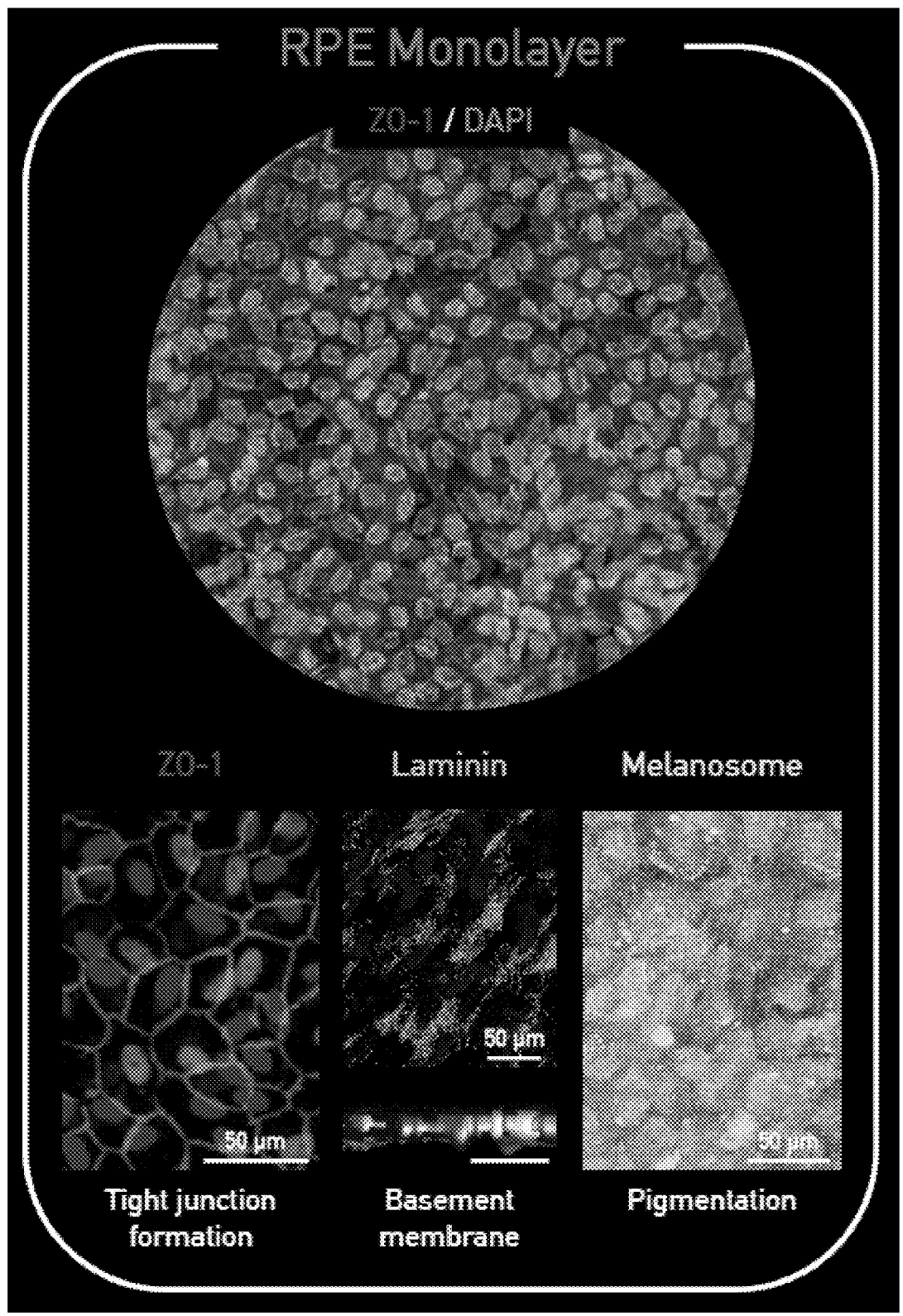
FIG. 6 illustrates the RPE monolayer and the related tight junction formation markers, basement membrane markers, and pigmentation markers.
Figure 7:
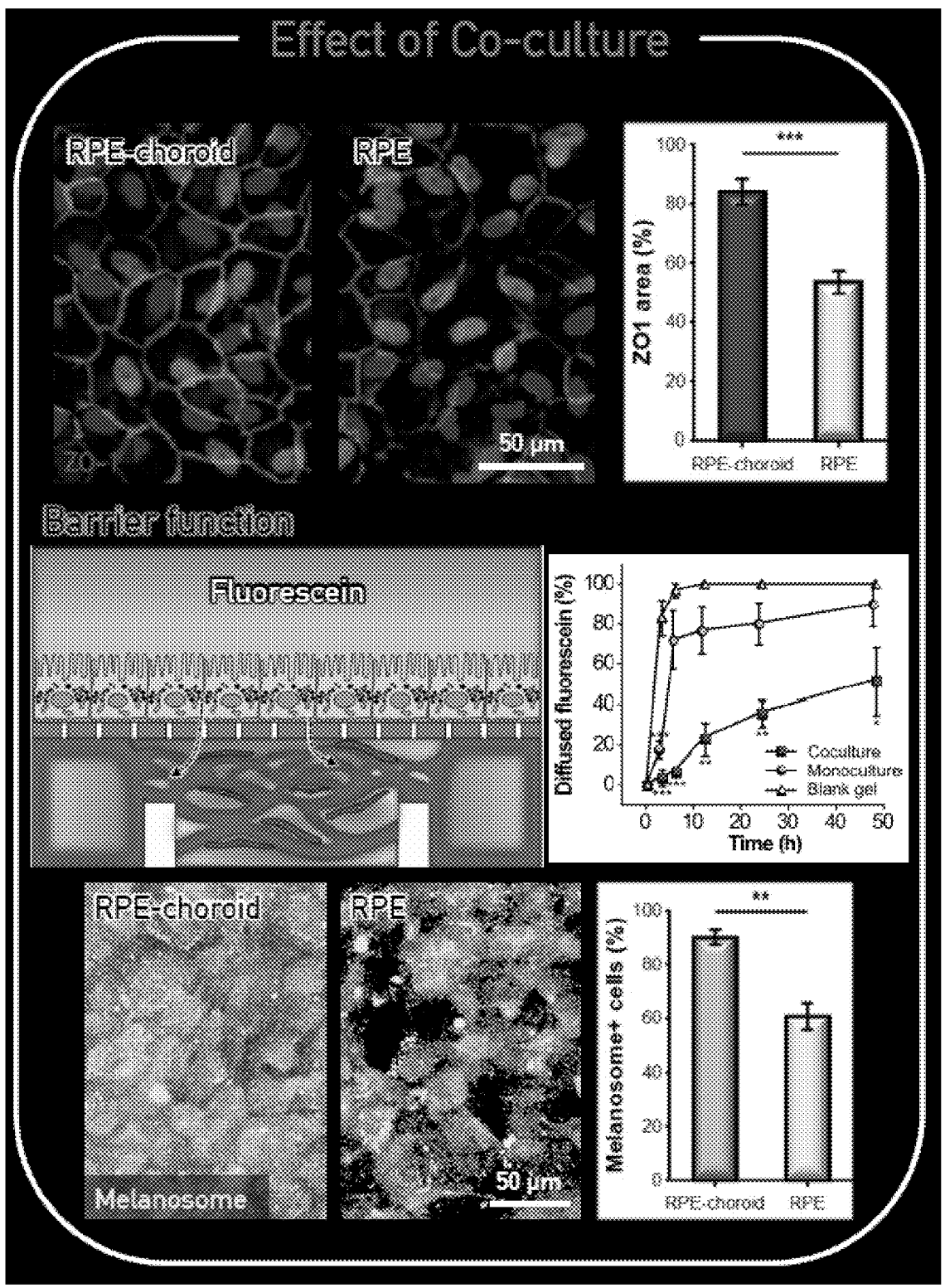
FIG. 7 illustrates the effect of co-culture.
Figure 8:
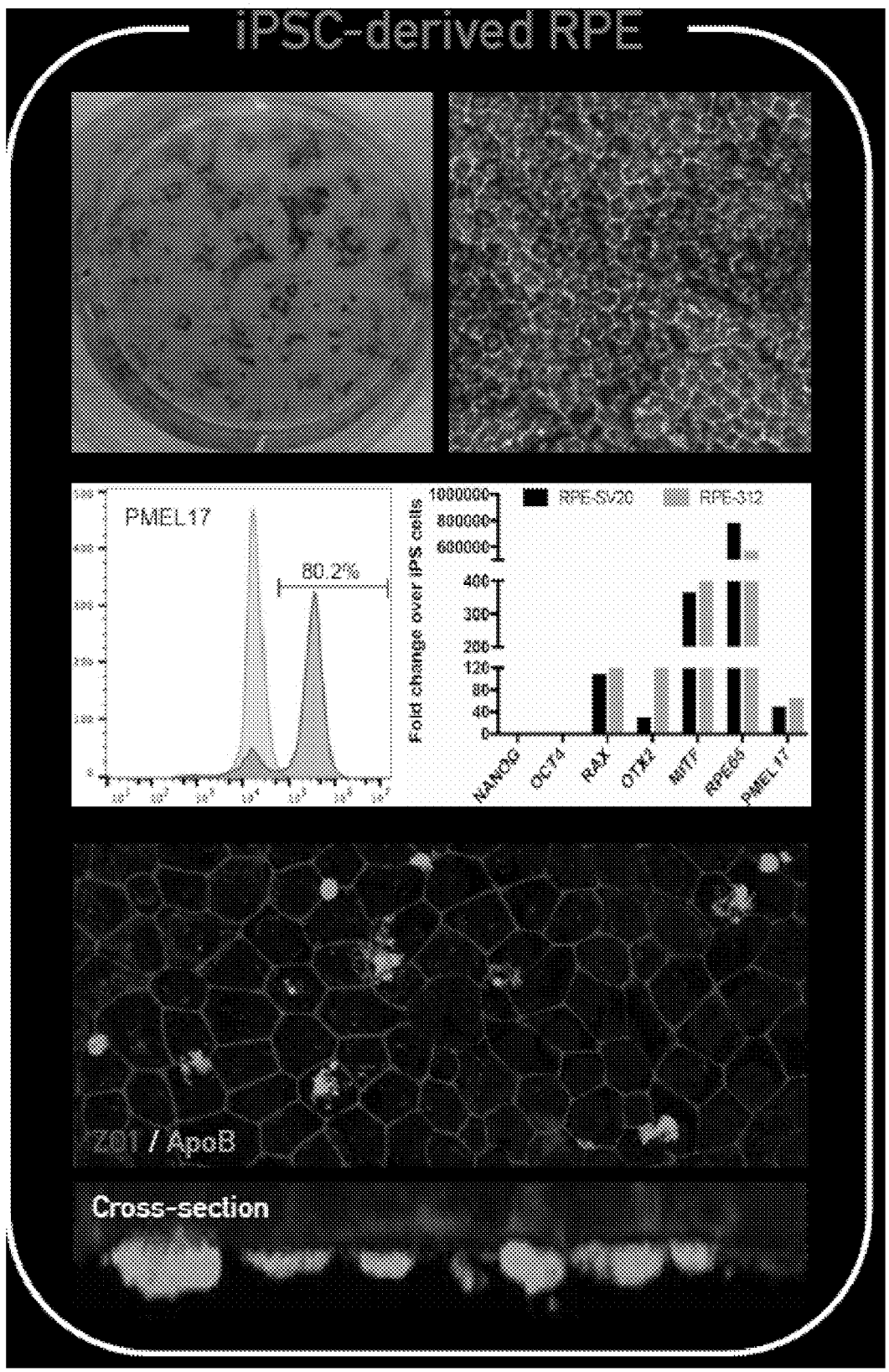
FIG. 8 illustrates the iPSC-derived RPE.
Figure 9:
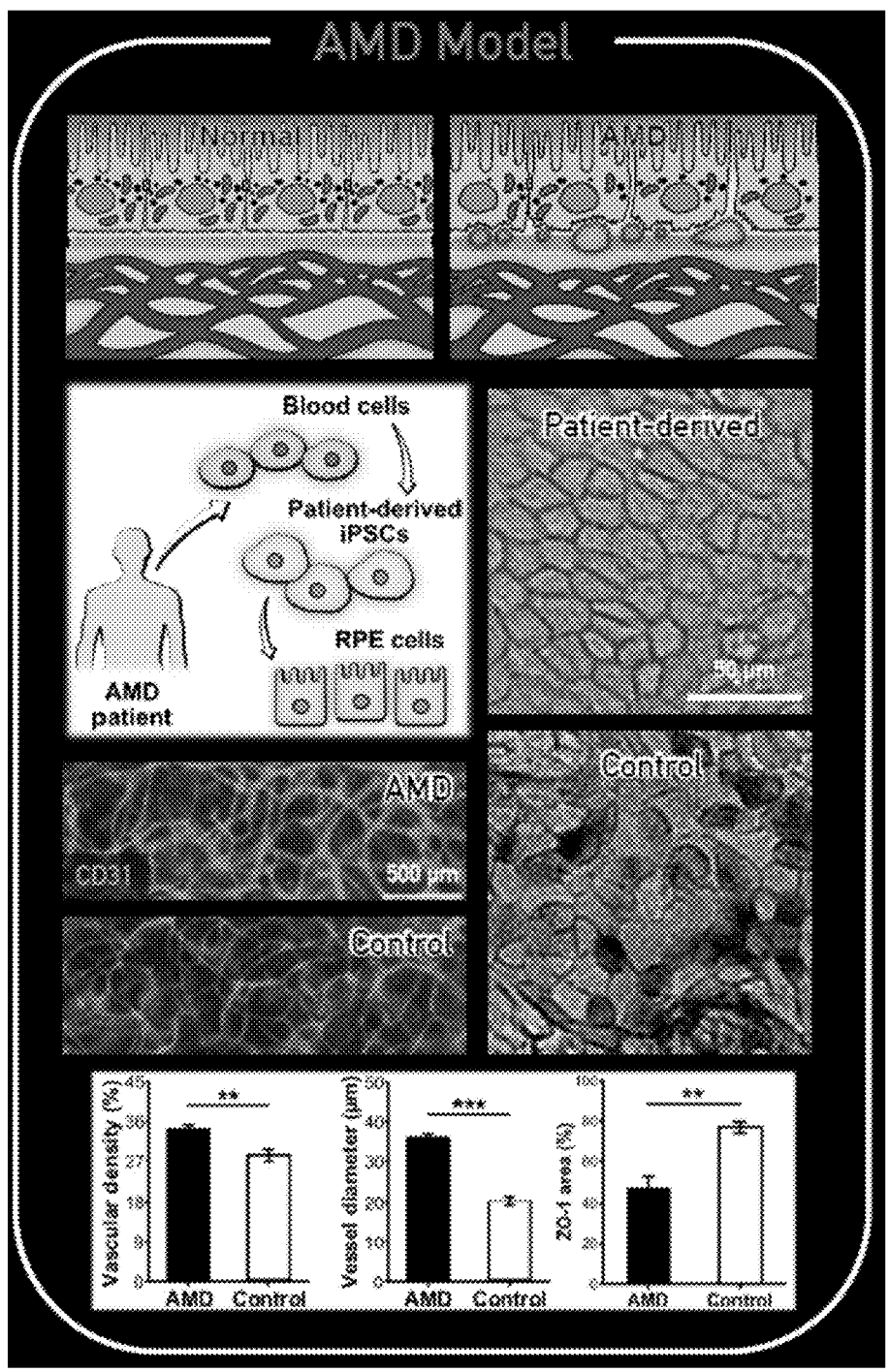
FIG. 9 illustrates the AMD model.
Figure 10:
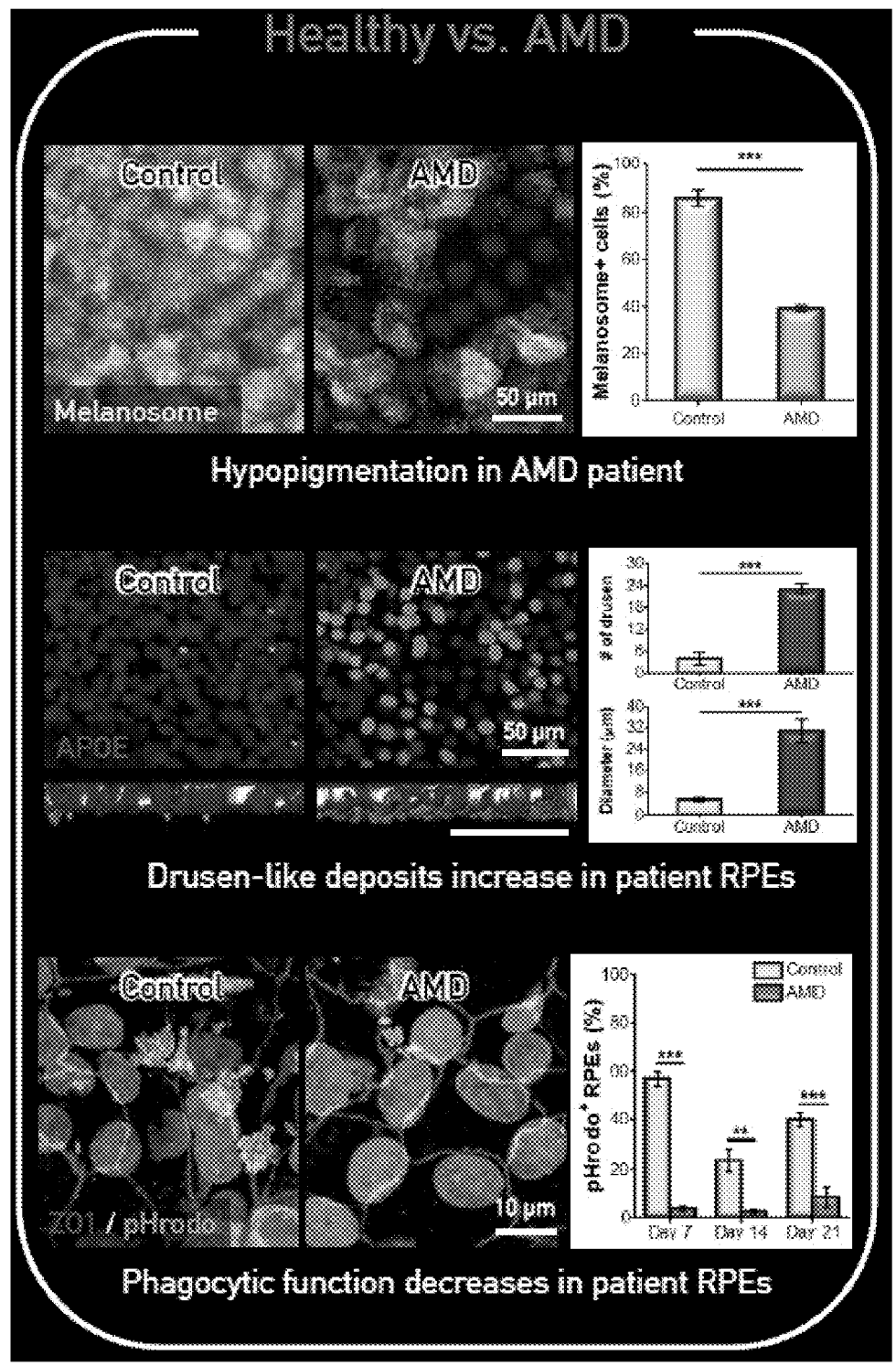
FIG. 10 illustrates the hypopigmentation, the increased Drusen-like deposits and the decreased phagocytic function in AMD patients.
Figure 11:
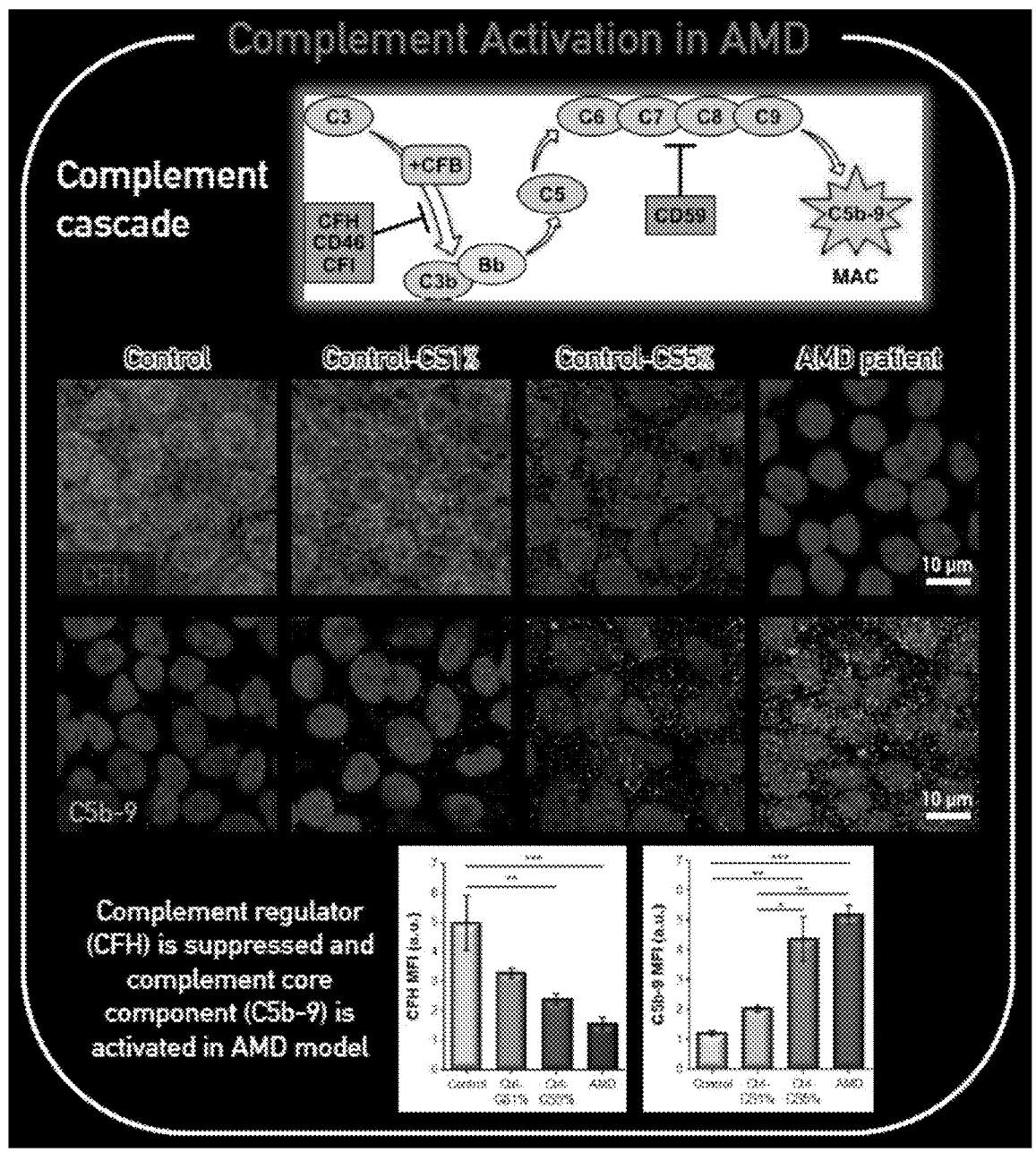
FIG. 11 illustrates complement activation in AMD.

This platform was used to culture RPEs differentiated from AMD patient-derived iPSCs with the goal of developing a pathophysiological model of AMD. Interestingly, these cells spontaneously showed hypopigmentation and downregulation of RPE65 expression and tight junction formation (FIG. 6). Another important finding was that the number and size of drusen-like deposits on the basolateral side were significantly increased in comparison to the control group established using normal iPSC-RPEs. Decreased laminin expression in the patient group also represented the remodeling of Bruch's membrane components in the disease state of AMD. In addition, the patient-derived cells showed increased barrier permeability and decreased phagocytic activities as compared to control.

Furthermore, it was demonstrated the potential of this model for the study of complement cascade during the progression of AMD. AMD is also considered as a chronic inflammatory disease as it is often related to defective or inappropriate regulation of the continuously activated alternative complement pathway. Using the presently disclosed model, it was mimicked the early stage of dry AMD by exposing control iPSC-RPEs to cigarette smoke. For this, cigarette smoke extract was perfused through the microengineered blood vessels to mimic the effect of cigarette smoking in the human body in which it is absorbed in the lung and travel through the blood stream to mediate toxic effects via increased production of oxidative stress in the outer blood-retinal barrier. Complement activation was compared between cigarette smoke exposed control and AMD groups to examine dysregulation of complement cascade. As a result, downregulation of complement inhibitory factors (e.g., complement factor H) was observed in both AMD and high cigarette smoke (5%) exposure groups (FIGS. 16A-16F). Importantly, ELISA analyses on some of the major complement cascades also indicated significant dysregulation of the complement pathway in patient and cigarette smoke groups.

The present example includes testing of the potential complement inhibitory drugs on the presently disclosed platform including AMD patient or cigarette smoke exposed RPE-choroid model to test therapeutic effects of drugs. Furthermore, engineering approaches described in the present disclosure provide numerous possible applications in the field of mimicking biological complexity of various organs and tissues by allowing two different cell culture layers in three-dimensional environment in both micro and macro scales.

Standard in vitro models for studying outer blood-retinal barrier or RPE-choroid complex involve culture of two or three different cell types (e.g., endothelial cells, fibroblasts, and RPEs) on semipermeable Transwell supports. However, these commercially available cell culture platforms are greatly limited in their ability to recapitulate complex three-dimensional structure and dynamic biological microenvironments that play an essential role in health and disease. The microengineered 3D cell culture model presented herein demonstrates the ability to model the RPE-choroid complex in a much more realistic manner than is possible using traditional in vitro techniques (e.g., Transwell inserts). As this model closely recapitulates the exact size of the human outer blood-retinal barrier (human macula diameter=5.5~6 mm, the present RPE culture diameter=6 mm; human choroid thickness=250~400 μm, the present blood vessel layer thickness=400 μm), this system serves as a robust research platform for studying the development and progression of AMD as well as for discovering potential drugs for AMD.

The 3D human blood-retinal barrier model can be further used to study molecular and cellular mechanisms underlying the pathogenesis of ocular diseases. Recently, microengineered organs-on-chips provided physiologically reliable in vitro biomimetic models that can be used in studies of cell biology and drug screening. Moreover, this platform provides new opportunities to develop patient-specific disease models by utilizing patient-derived iPSC-RPEs that can be used in a variety of biomedical, pharmaceutical, toxicological applications.

Another application of this model lies in the area of personalized medicine to provide an access to a patient's genetics and allow personalized evaluation of the safety and toxicity of environmental exposures (e.g., chemicals, toxins) and drugs in the events of retina-associated degenerative diseases. Currently, AMD can be diagnosed based on visual dysfunction and characteristic macular findings. However, progression of the disease can differ greatly from patient to patient and faster disease progression may lead to a vision loss in both eyes. This platform can serve as a personalized research tool to study interactions between components that consist blood-retinal barrier in the progression of disease states. Furthermore, by including additional tissue layers that mimic the inner retina (e.g., photoreceptors), it can further expand the applications of this model to the study of mutualistic relationship between the components of the retina (photoreceptors, RPEs, and choriocapillaris) at different states of ocular disease (e.g., AMD).

Example 2

Understanding the biology and pathophysiology of the blood-retina barrier (BRB) in the human eye has been challenged by the lack of physiologically relevant experimental models that recapitulate its three-dimensional (3D) architecture. The present disclosure addresses this limitation by applying organ-on-a-chip technology to engineer the human outer retina. To achieve the 3D configuration of BRB, a microengineered platform has been developed to allow for the prolonged culture of human retinal pigment epithelium (RPE) cells interfaced with perfusable vascular network. Compared to RPE monoculture, RPE cells co-cultured with blood vessels in the presently disclosed device show significantly enhanced pigmentation, barrier function, and phagocytosis, which are all necessary for the maintenance of tissue homeostasis in the retina. Using induced pluripotent stem (iPS) cell derived RPEs from healthy donors, a phenotypically and functionally mature BRB model that can be maintained for over 3 weeks is demonstrated herein. Furthermore, the present example shows the advanced capabilities of the presently disclosed system in disease modeling by incorporating iPS RPEs from age-related macular degeneration (AMD) patients to reproduce key pathological phenotypes of AMD, including hypopigmentation, increased drusen deposition, and compromised barrier and phagocytic functions. Finally, the present example studies the complement activation in RPEs after exposure to cigarette smoke extract and test the efficacy of complement-targeting therapeutic antibodies. This work suggests a significant improvement in our ability to model the human BRB and AMD-associated aberrations in vitro that could facilitate drug discovery. Age-related macular.

The human blood-retina barrier (BRB) in the eye is a physiological barrier composed of retinal pigment epithelial cells (RPEs) interfaced with the capillary bed of the choroid, and it controls nutrient transport between the blood and the inner retina to maintain homeostasis for normal retina function (FIG. 12A). Among the numerous barrier tissues in the human body, this tissue-tissue interface is virtually unique in that its establishment and maturation take place in utero and must remain viable throughout the lifetime to perform its array of functions. Specifically, RPE cells support the immune privilege of the eye by forming tight junctions to isolate the inner retina from the external influences and are densely packed with pigment granules that are responsible for absorbing scattered light. The choriocapillaris provides signals and transports nutrients that are required for maturation of the RPE cells and is also required to maintain BRB regulation and integrity. The BRB is also of major clinical relevance because dysfunction of the BRB is observed in many eye diseases including age-related macular degeneration (AMD), diabetic retinopathy, and other chronic retinal diseases. With the increasing attention to the novel therapeutics for such diseases, various in vivo and in vitro models have been developed to investigate the structure and function of BRB in diseased conditions.

Despite the opportunity animal models have offered to better understand the biology and pathophysiology of the BRB, their use in modeling human BRB is not without limitations. For example, rodent models of AMD have revealed many important aspects of the underlying pathology of the disease; however, they are still limited by the anatomical lack of the macula, which might explain why none of these models have yet been able to capture the complexity of progression from early to late AMD. More importantly, animal models may not accurately mimic the gene expression changes observed in human, making their use for the evaluation of potential therapeutics problematic. While this problem can be solved by using human cell culture models, many of the early studies have focused on incorporating primary human fetal RPE cells or the immortalized ARPE-19 cell line to simulate the tissue physiology and pathology of BRB. Although these models have advanced the understanding of RPE cells in the human BRB, existing in vitro models are greatly limited in their ability to meet the need to expand the research scope to the tissue and organ levels. For example, two-dimensional (2D) monolayer of RPE cells fails to represent the higher-level architecture of the in vivo BRB, which is characterized by a complex three-dimensional (3D) structure of RPE and choroidal vessels. This limitation is particularly problematic in modeling the salient features of AMD as the interaction between the RPE cells and the subepithelial blood vessels plays an essential role in the development and progression of the disease. Conventional approaches to co-culture RPE cells and endothelial cells in Transwell inserts also present major challenges in reconstituting the structural and functional integration of the BRB in an organ-specific manner. Therefore, new practical approaches are needed to develop a human BRB model that exhibits physiologically relevant structure and function.

The present example demonstrates the feasibility of engineering an advanced in vitro platform to address these important drawbacks of previous BRB models by fully recapitulating the inherent complexity of BRB in an integrated physiological context. This approach utilizes a 3D culture platform to generate RPE monolayer in a chamber with the same size as the human macula. Moreover, it was implemented a microfabrication technique to create microfluidic channels that can be used to form perfusable 3D vascular network in an extracellular matrix (ECM) hydrogel scaffold to realistically model the microvasculature in BRB. For this purpose, human vascular endothelial cells and fibroblasts were co-cultured in ECM hydrogel to emulate the de novo vasculogenesis process and induce spontaneous formation of vascular network throughout the scaffold. The present example describes the basic principle of the presently disclosed 3D culture approach by demonstrating prolonged culture of primary human RPE cells and blood vessels to develop a human BRB-on-a-chip. The present example shows that the resulting BRB tissue construct exhibits structural and functional integrity during the extended culture period. Furthermore, the present example demonstrates the advanced capabilities of the presently disclosed subject matter in modeling BRB using human induced pluripotent stem cell (iPSC)-derived RPE cells to engineer an in vitro model with a potential application in precision medicine. In addition, the present example shows AMD-on-a-chip by culturing AMD patient-derived iPS-RPE cells that carry phenotypic and genetic variants associated with the disease. The feasibility of using this system to simulate complement activation in AMD by exposing RPE cells to cigarette smoke extract through vascular perfusion is also demonstrated. Finally, the presently disclosed AMD-on-a-chip was used to study the efficacy of complement-targeted therapeutic antibodies that are currently being evaluated for clinical use for the treatment of AMD.

A microengineered cell culture device made out of poly (dimethylsiloxane) (PDMS) that enables the production and maintenance of a multi-layer tissue construct of the BRB (FIG. 12B). This BRB chip consists of an upper RPE chamber (shown in blue) separated from vascular microchannels (shown in red) by a porous membrane (FIG. 12B). To make this device, a bottom PDMS layer containing microfabricated channel features is bonded to a porous membrane, which is bonded to a top PDMS layer (FIG. 12C). In the first step of establishing cell culture in this device, primary human endothelial cells and fibroblasts are suspended in an ECM hydrogel precursor solution and injected into the bottom vascular microchannel (FIG. 12D). During this process, surface tension acts to pin the meniscus of the solution at the edge of the microfabricated features called steps, allowing the injected hydrogel to fill the entire channel without spillage (FIG. 12D). After formation of a cell-laden hydrogel scaffold, the parallel side microchannels are seeded with endothelial cells to form an endothelium on the luminal surface (FIG. 12D). Simultaneously, the upper RPE chamber is seeded with primary human RPE cells to form an epithelial monolayer (FIG. 12D). Then, culture medium is added to the device to provide nutrient supply to the cells. Confocal immunofluorescence microscopic analysis after 10 days of culture revealed that these conditions resulted in the formation of a RPE monolayer interfaced with a vascular network as visualized by expressions of the RPE (RPE65) and endothelial cell (CD31) markers, recapitulating the 3D architecture of the human BRB (FIG. 12E). For the formation of vascular beds, the endothelial cells cultured in the hydrogel scaffold underwent proliferation and self-assembly over a period of 7 days, approximating vasculogenesis in vivo to develop a network of microvessels (FIG. 12F).

Figures 12I, 12J, 12K, 12L:
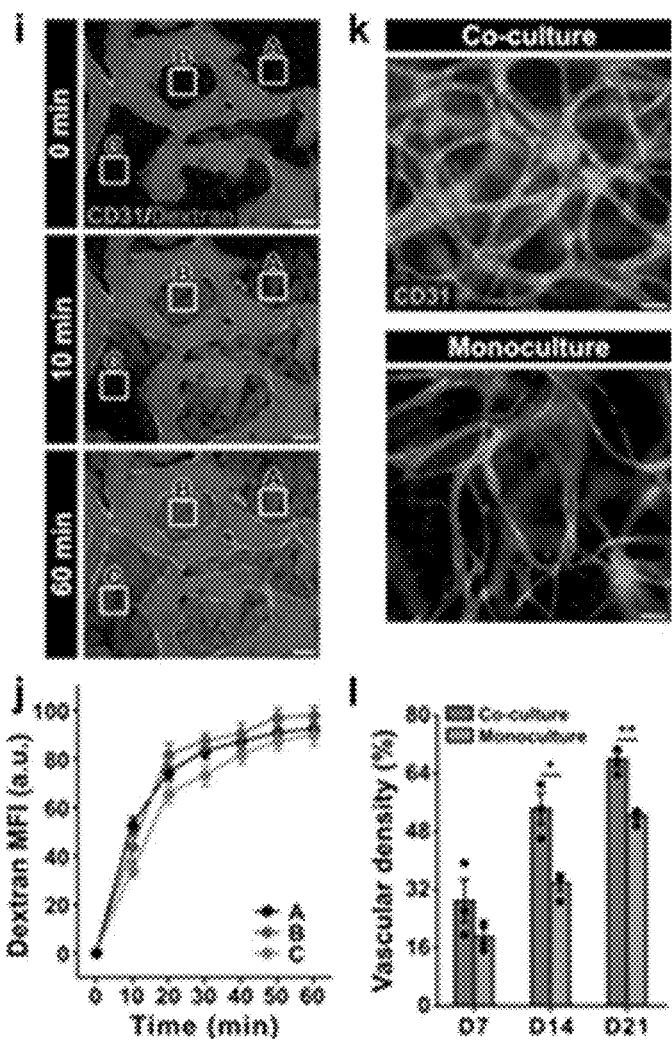

In the eye, the choroid is primarily a vascular structure that supplies nutrients to the retina by facilitating transport across the RPE. Following this tissue structure and function, it was investigated whether the engineered vasculature formed in the hydrogel scaffold established a perfusable network to the microchannels. To examine the perfusability of the microvessels, a fluorescently labeled solution containing 70 kDa FITC-dextran was injected into one of the endothelialized side channels. Under this condition, the solution was observed to enter the microvessels and flow in the direction of applied pressure gradient, eventually reaching the other vascular microchannel (FIG. 12G). During flow, the dextran solution was retained in the intravascular space without leaking into the surrounding scaffold, illustrating the vascular integrity of the engineered vessels (FIG. 12H). A similar experiment was performed using 1 μm fluorescently labeled microbeads to show a continuous flow of the particles through the vascular network. Next, it was whether the microengineered vascular network allows diffusive transport of soluble factors. In the retina, oxygen and other nutrients diffuse from the choroidal capillary walls to the inner retina by crossing the blood-retina barrier. To examine this vascular function, temporal changes in the intensity of dextran solution (70 kDa) passively diffusing into the perivascular space of the hydrogel scaffold were measured. For spatial analysis, these measurements were taken at three different locations (regions A, B and C) (FIG. 12I). In all three locations, dextran diffusion into the perivascular space was evident from the increase in fluorescence intensity within 30 min without significant spatial variability (FIG. 12J). These results clearly demonstrate the perfusability and diffusibility of the microengineered 3D vasculature in the presently disclosed model, making the presently disclosed platform attractive for recapitulating the structure and function of the native vasculature.

Interestingly, the process of vasculogenesis occurred in a RPE-dependent manner. When the engineered vessels were cultured alone without RPEs, the vascular density was significantly reduced as compared to that measured in the co-culture system at the same time points (FIG. 1k,l). It was observed that the RPEs have the capacity to secrete vascular endothelial growth factor (VEGF), a signaling protein that promotes the growth of vessels, which may have played an important role in the formation and maintenance of microengineered vessels in the presently disclosed model. This result illustrates significant RPE contributions to vessel formation.

Figures 13A, 13B, 13C, 13D, 13E, 13F:
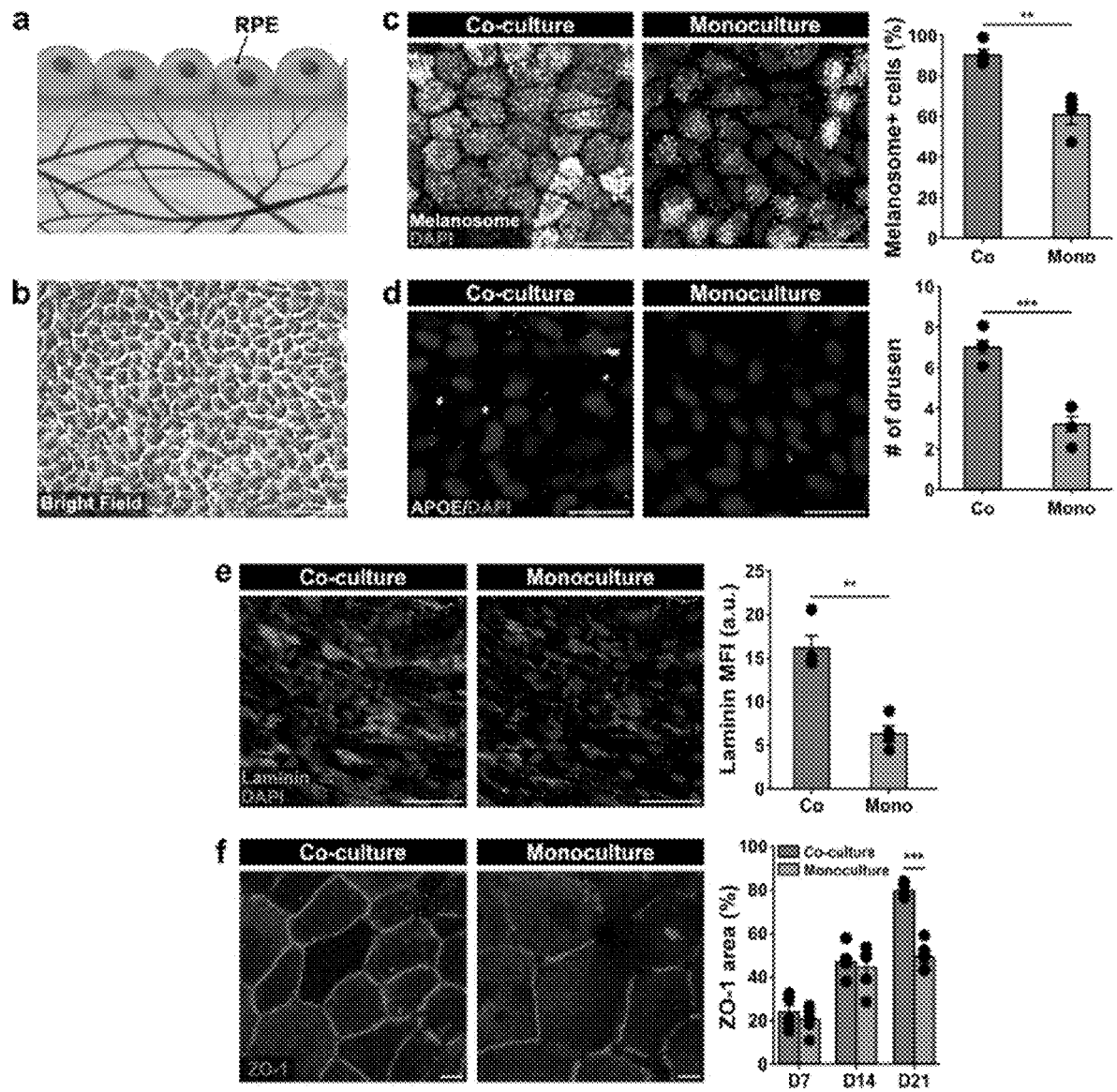
FIGS. 13A-13H illustrate characterization of human RPE tissue on a BRB chip.

Next, the capabilities of the presently disclosed organoid were leveraged to examine the effect of microengineered vasculatures on the maturation of the retinal pigment epithelium. As the major site of light absorption in the human eye, RPE is composed of highly pigmented cells that form a tight barrier and transport nutrients, ions, and water to the inner retina (FIG. 13A). Conventionally, the study of RPE has relied predominantly on the monolayer culture of RPE cells. This traditional model, however, is greatly limited in its ability to recapitulate structural and functional coupling of RPEs with the vascular bed that plays a critical role in the physiological maturation and function of RPEs. In particular, the BRB consists of highly vascularized choroid tissue and relies on this vasculature for the transport of nutrients, oxygen, and various soluble factors to maintain tissue homeostasis and carry out its specialized functions. Studies have also shown that the development and repair of RPE occur in coordination with the underlying vasculature. Despite the increasing recognition of the vasculature as a critical component of BRB, modeling this essential feature using traditional in vitro techniques remains a significant challenge.

To suggest an advanced in vitro strategy to tackle this problem, the presently disclosed BRB chip was used to study the effect of microengineered vessels on the maturation of RPE cells (FIG. 13B). First, RPEs and microvasculature were co-cultured for extended periods (over 21 days) to establish the complete BRB model. Then, it was examined the development of dark granules in the cytoplasmic compartment of RPEs based on previous genetic and immunological studies showing that the appearance of pigmentation is an indicator of RPE differentiation and maturation. Interestingly, more than 90% of RPEs in the presently disclosed co-culture model appeared to be melanosome-expressing cells, suggesting robust synthesis of pigment melanin in the presence of microvasculature (FIG. 13C). In comparison to the co-culture model, when RPEs were cultured alone, this effect was significantly reduced as evidenced by less melanosome-positive cells. These results indicate pigmentation of the cultured RPEs in the presently disclosed BRB model, which is an important characteristic of their in vivo counterparts that allows the RPEs to absorb scattered light and thus protects the retina from photo-oxidative stress. This characterization also revealed the production and deposition of small drusen-like deposits (APOE) on the basolateral side of the RPE monolayer (FIG. 13D). Importantly, this accumulation of extracellular deposit that built up underneath the RPE occurred in a vasculature-dependent manner. When the RPEs were cultured alone without the engineered vessels, the number of drusen-like deposits was reduced by 50% as compared to that measured in the co-culture model at the same point (FIG. 13D). Although the source of the proteins and lipids in drusen is suggested to be extracellular waste of RPEs and photoreceptors, previous studies suggest that the choroid is also likely to contribute to their formation, highlighting the importance of vascular components for the induction of physiological metabolism in RPEs to eliminate wastes. Similar to drusen-like protein deposition, RPEs deposit fibrous extracellular matrix proteins called laminin to form a thin sheet in the basal lamina, mimicking a Bruch's membrane in vivo. When the RPEs were cultured alone without the engineered vessels, the extent of laminin deposition was reduced by 60% as compared to that measured in the co-culture system (FIG. 13E), illustrating significant vascular contributions to basement membrane formation in the presently disclosed model. Although the relevance of these finding to the in vivo context needs to be validated, this observation raises the possibility that the mutualistic interaction between the RPE and choroid may play an important role in the development and maturation of RPEs.

Figure 13G:
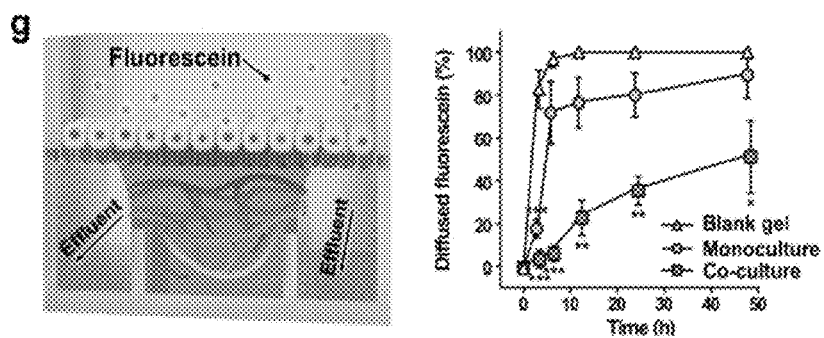

These results led us to hypothesize that this culture system allows for functional maturation of RPEs. To verify this hypothesis, it was measured the structural integrity of the epithelial barrier by immunostaining intercellular tight junction protein-1 (ZO-1), which is a critical feature of the retinal pigment epithelium in vivo that regulates the physiological barrier function of the BRB. Similar to pigmentation and laminin deposition, the expression of ZO-1 was significantly upregulated by prolonged coculture of RPEs with the underlying microvasculature (FIG. 13F), highlighting the importance of vascular components for the formation of complex, dynamic structures in RPEs. Given that the tight junctions in RPEs enable the epithelial monolayer to form a barrier and regulate diffusion through the paracellular spaces, it was next investigated transepithelial diffusion by measuring temporal changes in the relative intensity of fluorescein diffusing into vascular microchannels. In this analysis, cells were cultured and maintained in this BRB chip for 21 days, which was then exposed to fluorescein solution at the apical surface of the RPEs for 48 hours (FIG. 13G). The effluent was collected from the bottom vascular microchannels at different time points and the relative fluorescence intensity was calculated. In RPE monoculture devices, dysregulated transport of fluorescein into the bottom vascular channels was evident from the rapid increase in fluorescence intensity within 6 hours comparable to that measured in the blank gel, indicating the compromised barrier integrity of RPEs (FIG. 13G). Importantly, this significant diffusion was not observed in co-culture devices in which fluorescein diffusion occurred slowly over the period of 48 hours (FIG. 13G). In this case, the temporal profile of fluorescence intensity in the vascular microchannels was maintained below 60%, illustrating the intact barrier function of RPEs in the presence of engineered vessels (FIG. 13G).

Figure 13H:
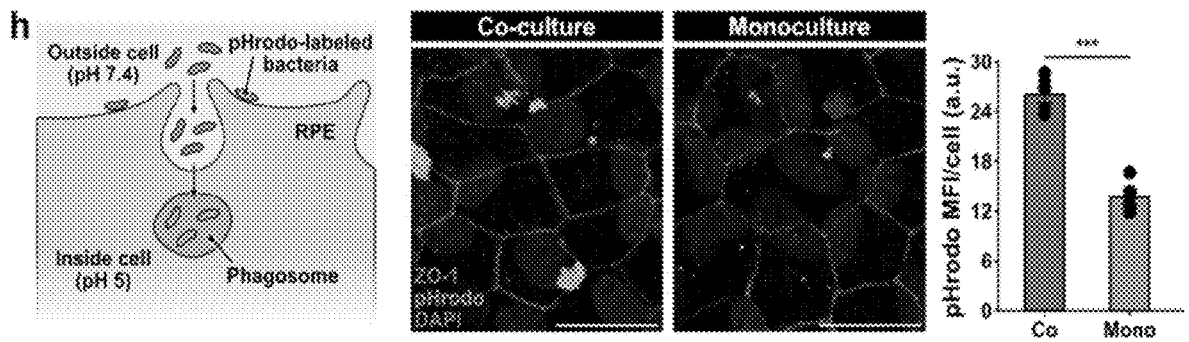

For further functional characterization, it was then used fluorescently labeled pH-sensitive dye (pHrodo) to visualize phagocytosis, which is another critical function of RPEs to maintain the visual cycle in the retina by renewing shedding photoreceptor outer segments. When bioparticles labeled with pHrodo dye are added to cells, the ones that are taken up by RPEs via phagocytosis become encapsulated in vesicles where pH decreases resulting in the fluorescence of pHrodo-labeled particles (FIG. 13H). Considering the intercellular cellular variability in phagocytic activity, it was measured the mean fluorescence intensity from representative RPEs selected for analysis. Upon treatment with pHrodo bioparticles, the expression of pHrodo fluorescence in RPEs was significantly increased in this co-culture device (FIG. 13H). The response of the monoculture model to the same stimulation occurred to a lesser extent (FIG. 13H), revealing that phagocytic activity in RPEs is greatly influenced by the vascular component. These findings suggest that this BRB chip significantly enhances the development of RPEs, allowing them to reach higher levels of phenotypical and functional maturity that play a central role in the barrier function of the retina.

Traditionally, in vitro modeling of RPE monolayer has used immortalized cell line (ARPE-19) or primary RPEs from donor tissues to understand ocular biology and diseases. While primary RPEs have the capacity to exhibit in vivo-like characteristics, they are difficult to source in large quantities from the same donor. In addition, it is very challenging to obtain cells from patients and they often have a limited ability to proliferate and maintain a polarized, cobblestone morphology, making a standardized disease model difficult to establish. To meet this challenge, efforts have been made to develop human induced pluripotent stem cell (hiPSC)-derived RPEs in which all the genetic and functional characteristics of an individual donor are retained. Inspired by this emerging body of work, it was explored the possibility of combining hiPSC-derived RPE monolayer with microengineered vasculature to establish an advanced human BRB tissue construct.

Figure 14A:
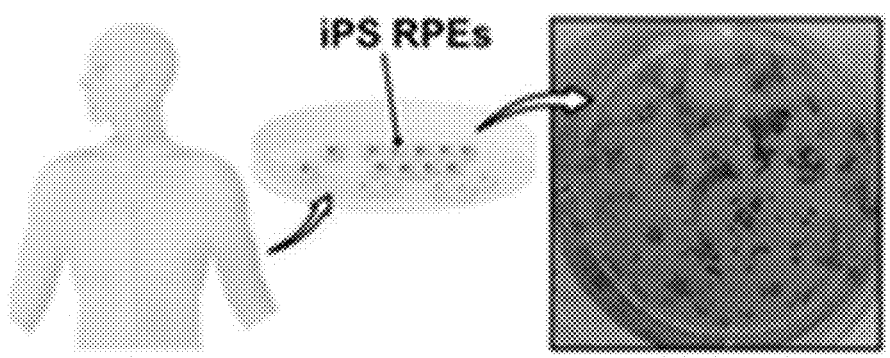
FIGS. 14A-14I illustrate a microengineered model of the BRB using human iPSC-derived RPEs.
Figure 14B:
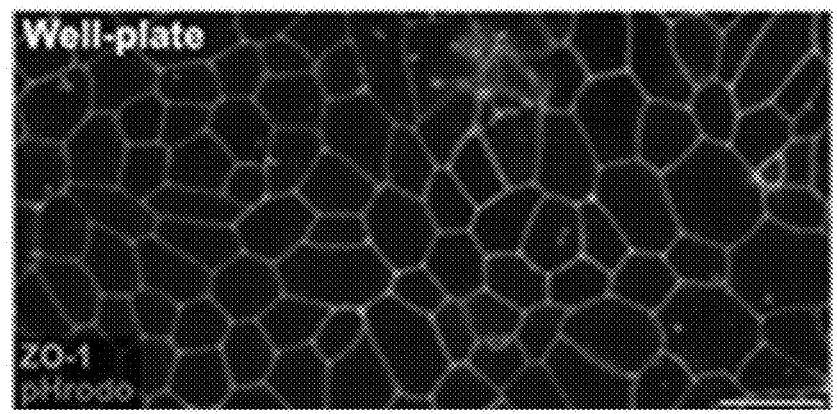

To create a BRB model using hiPSC-RPEs, adult cells donated from unaffected individuals were cultured and reprogrammed to generate two hiPSC lines from two unaffected controls. During culture, all iPSC lines showed typical hiPSC morphology and expressed the pluripotency markers in a manner described by the previous studies. These hiPSC lines underwent differentiation to produce RPE cells using previously published protocol, and the RPE colonies were then manually picked and passaged to obtain sufficient pure RPE cells. The resultant monolayer of iPS-RPEs expressed markers of mature RPE including OTX2, CRALBP and MCT1. Immunostaining with ZO-1 and pHrodo revealed that the iPS-RPEs had a typical cobblestone morphology with tight junctions and showed phagocytic functions, confirming that hiPSCs had been successfully differentiated into a RPE monolayer (FIG. 14B).

Figure 14C:
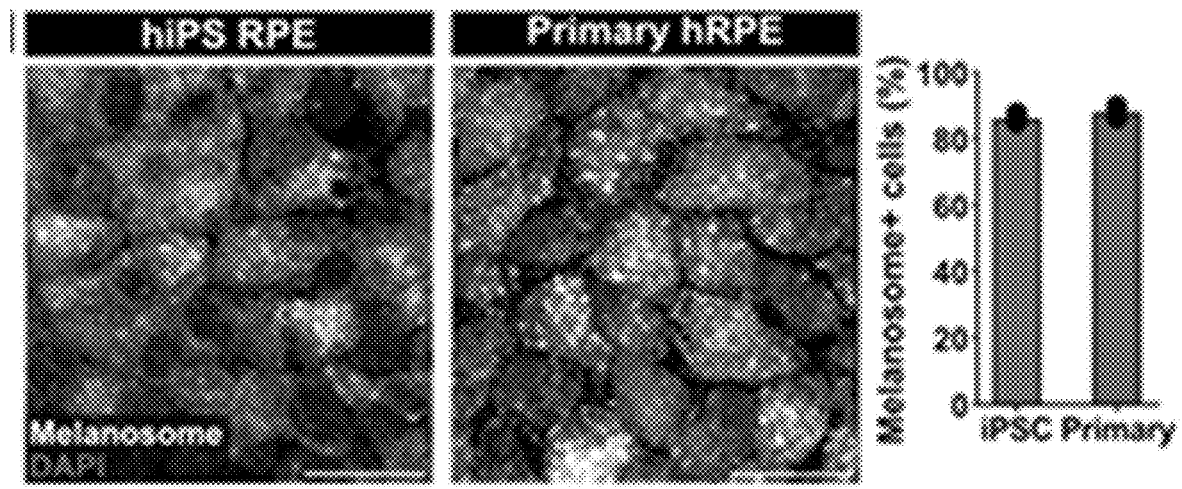
Figure 14D:
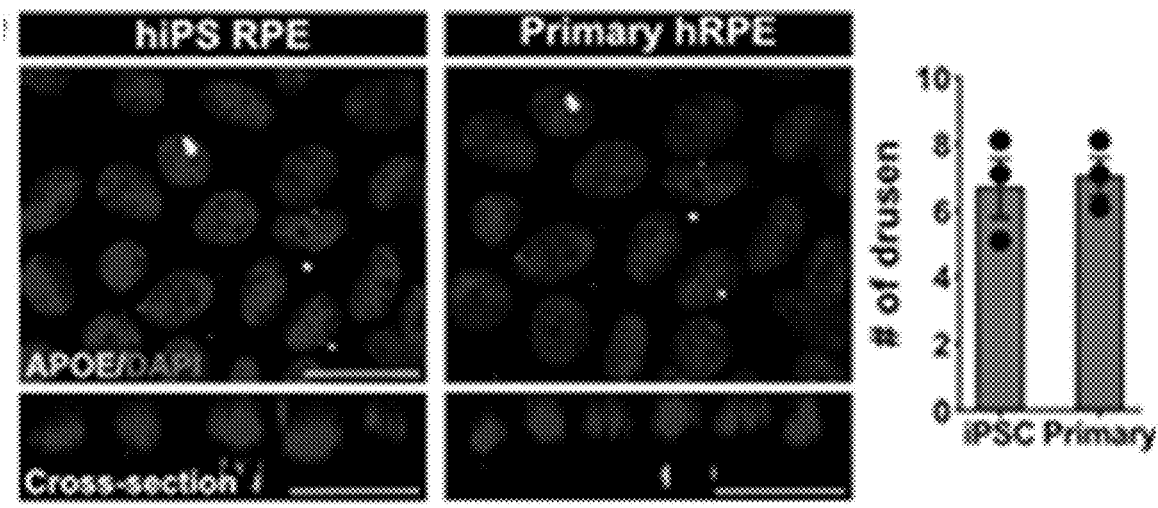
Figure 14E:
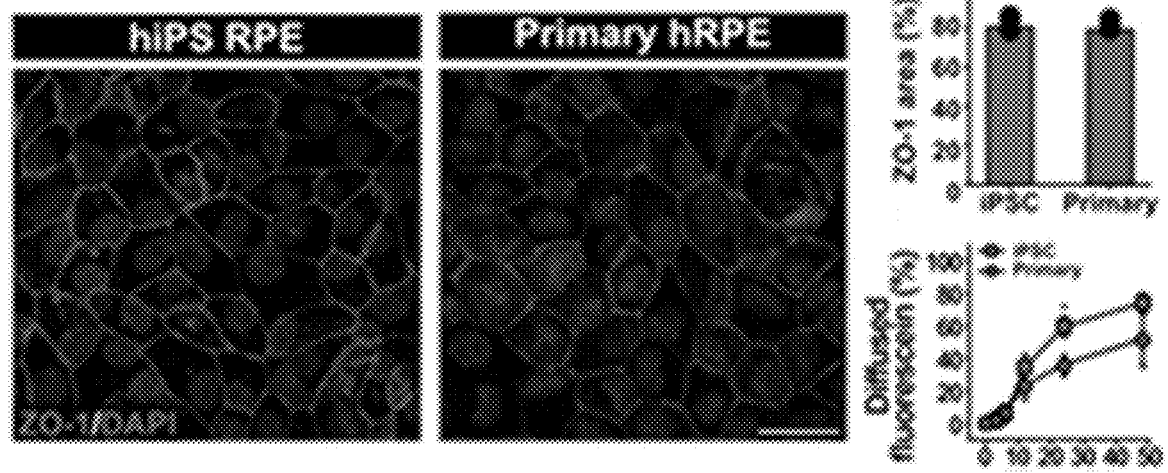
Figure 14F:
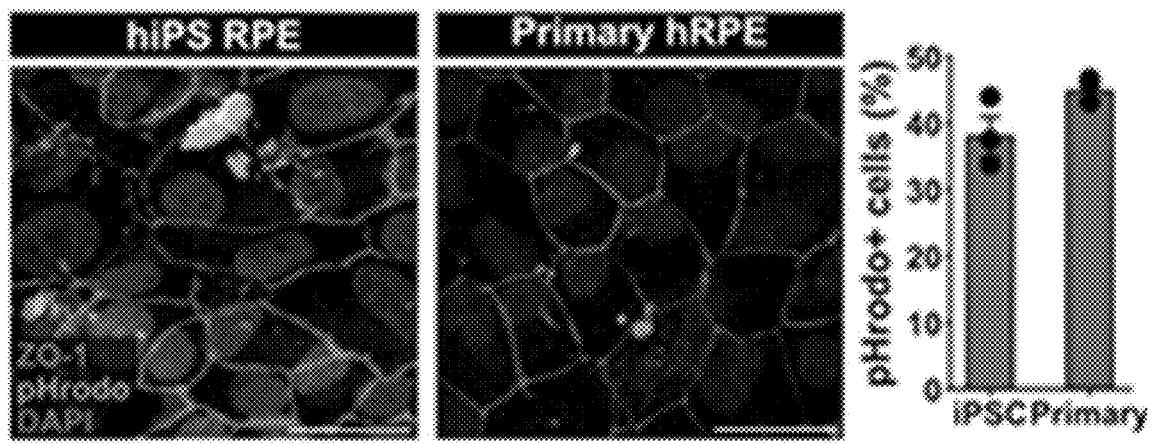
Figure 14G:
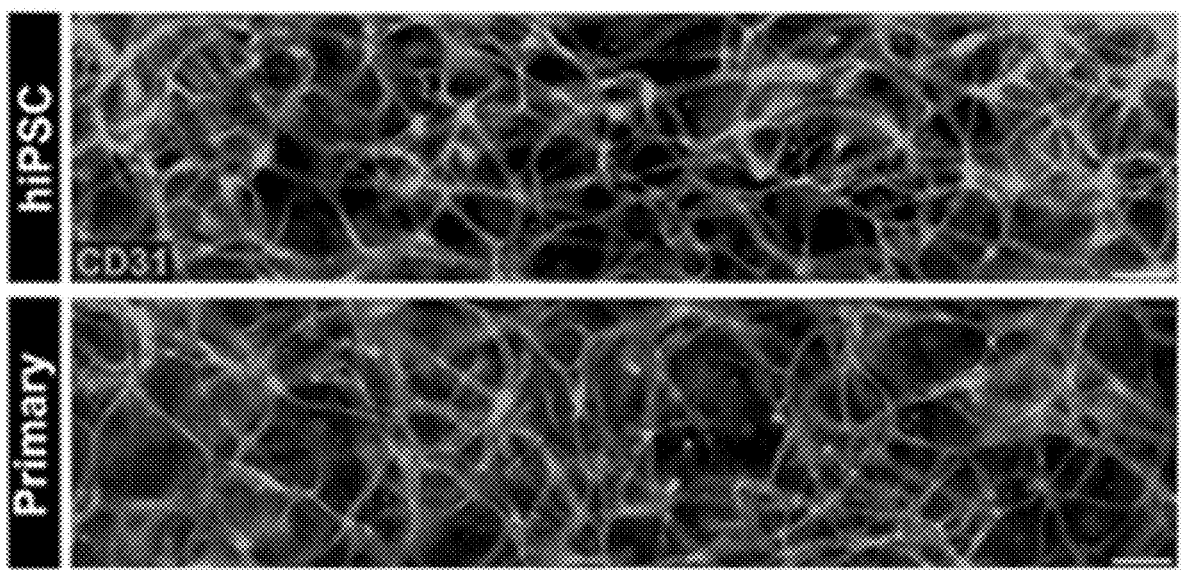

Next, the structural and functional characteristics of iPSC-RPEs with primary RPEs on this BRB chip were compared to determine whether iPSC-RPEs develop into a mature epithelial monolayer. To assess the level of pigmentation, the RPEs were immunostained with an anti-melanosome antibody and their mean fluorescence intensity measured after 21 days of culture. Immunostaining analysis did not reveal any difference in the expression of melanosome between iPS-RPEs and primary RPEs (FIG. 14C). For further phenotypical characterization, it was then assessed the sub-epithelial accumulation of drusen-like deposits. Upon culture with engineered vasculature, small numbers of drusen-like deposits were observed at the basolateral side of iPS-RPEs in a similar manner observed in primary RPEs at the same timepoint (FIG. 14D). Moreover, when immunostained with ZO-1 antibody to visualize tight junction formation, iPS-RPEs in BRB chip showed robust expression of tight junction protein without noticeable difference compared to primary RPEs (FIG. 14E). Further analysis also revealed that iPS-RPE monolayer maintained its barrier function in a similar extent to the primary RPE monolayer over a prolonged culture period (FIG. 14F). It was noted that the iPS-RPEs show comparable robust phagocytic activity to primary RPEs after 21 days of co-culture with vasculature (FIG. 14G).

Figure 14H:
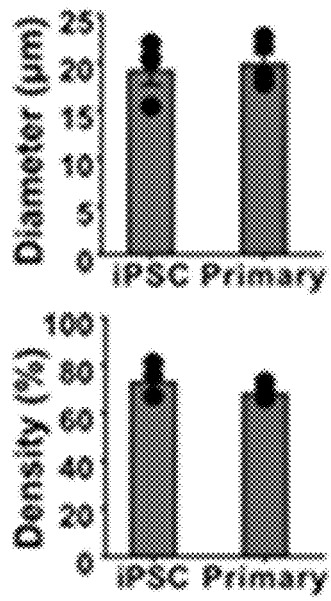
Figure 14I:
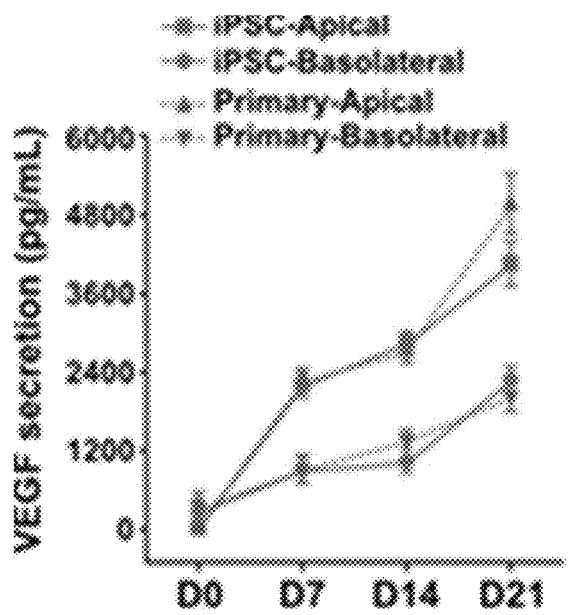
Figures 15A, 15B, 15C:
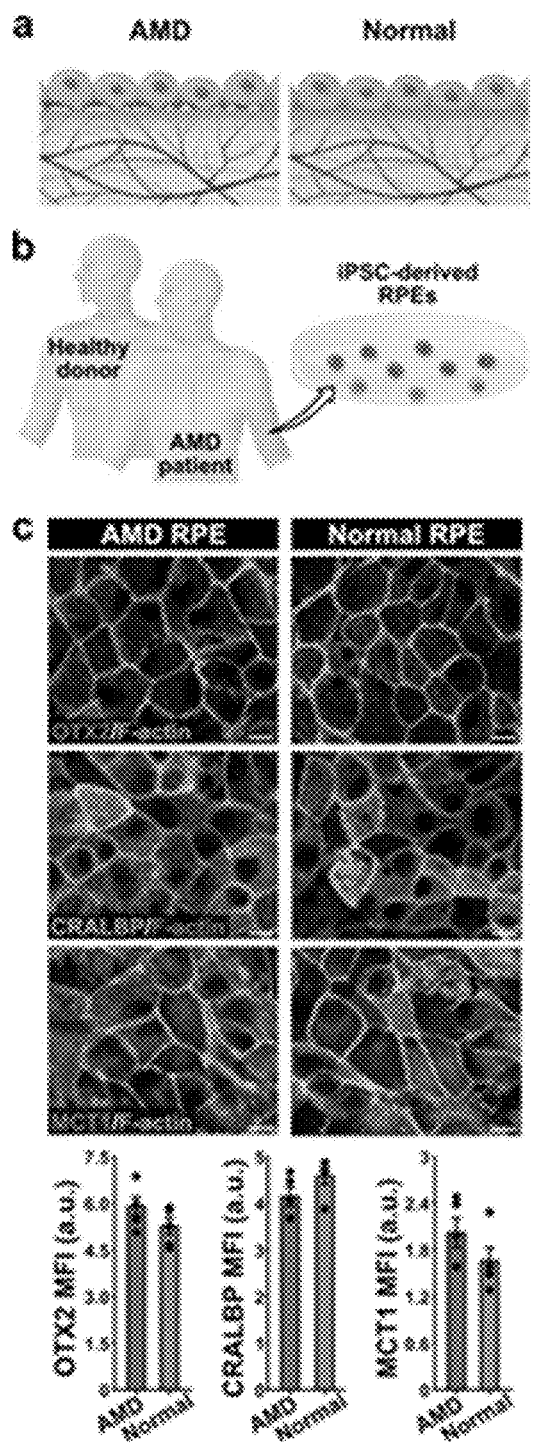
FIGS. 15A-15M illustrate a AMD model on a BRB chip.
Figures 15D, 15E, 15F, 15G:
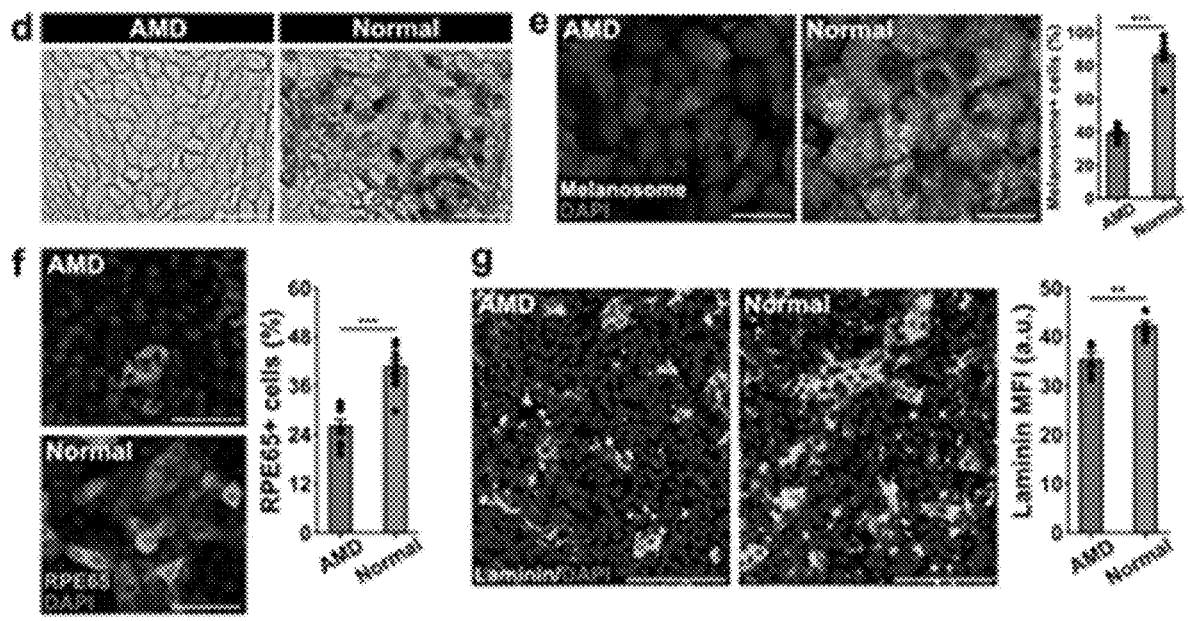
Figure 15H:
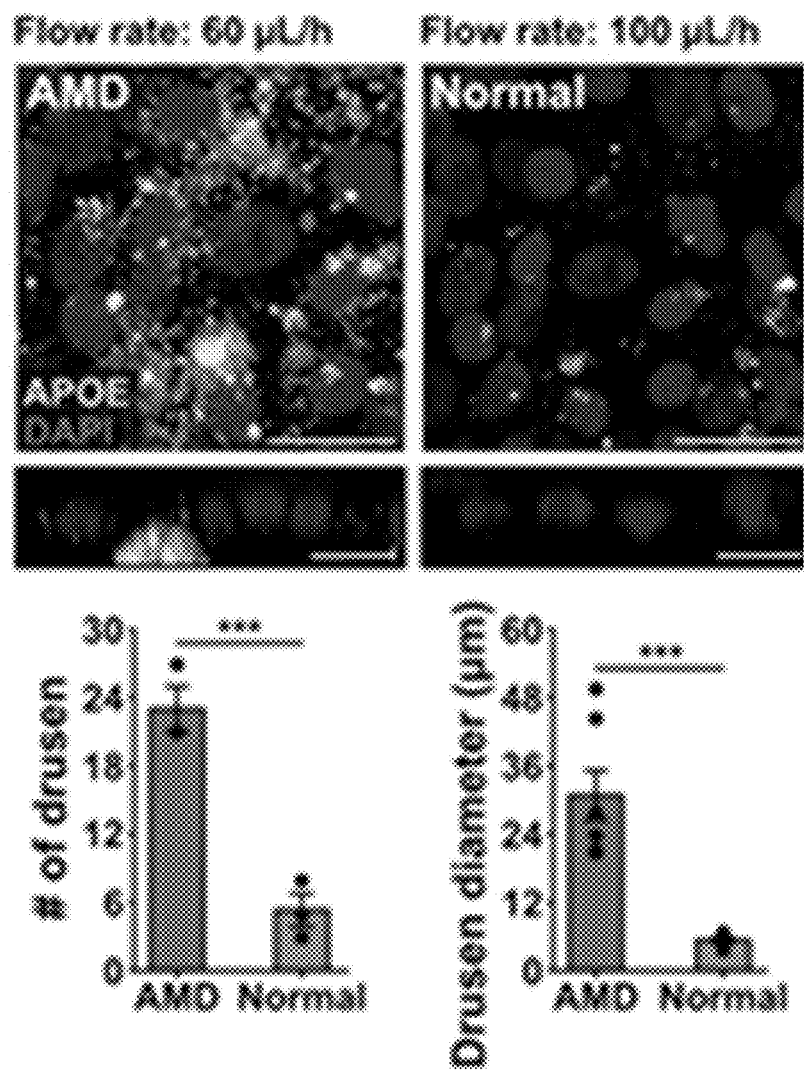
Figures 15I, 15J:
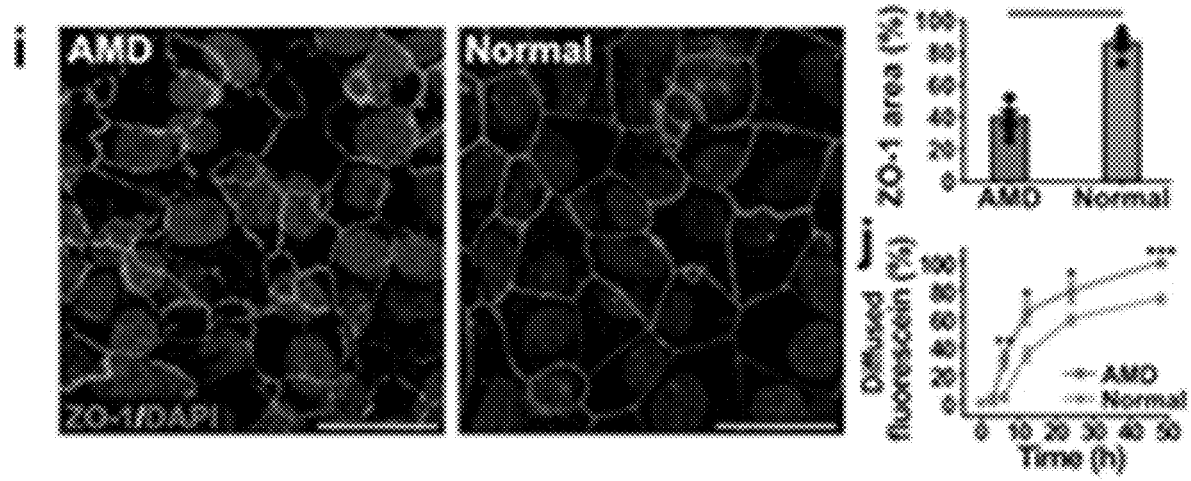
Figures 15K, 15L, 15M:
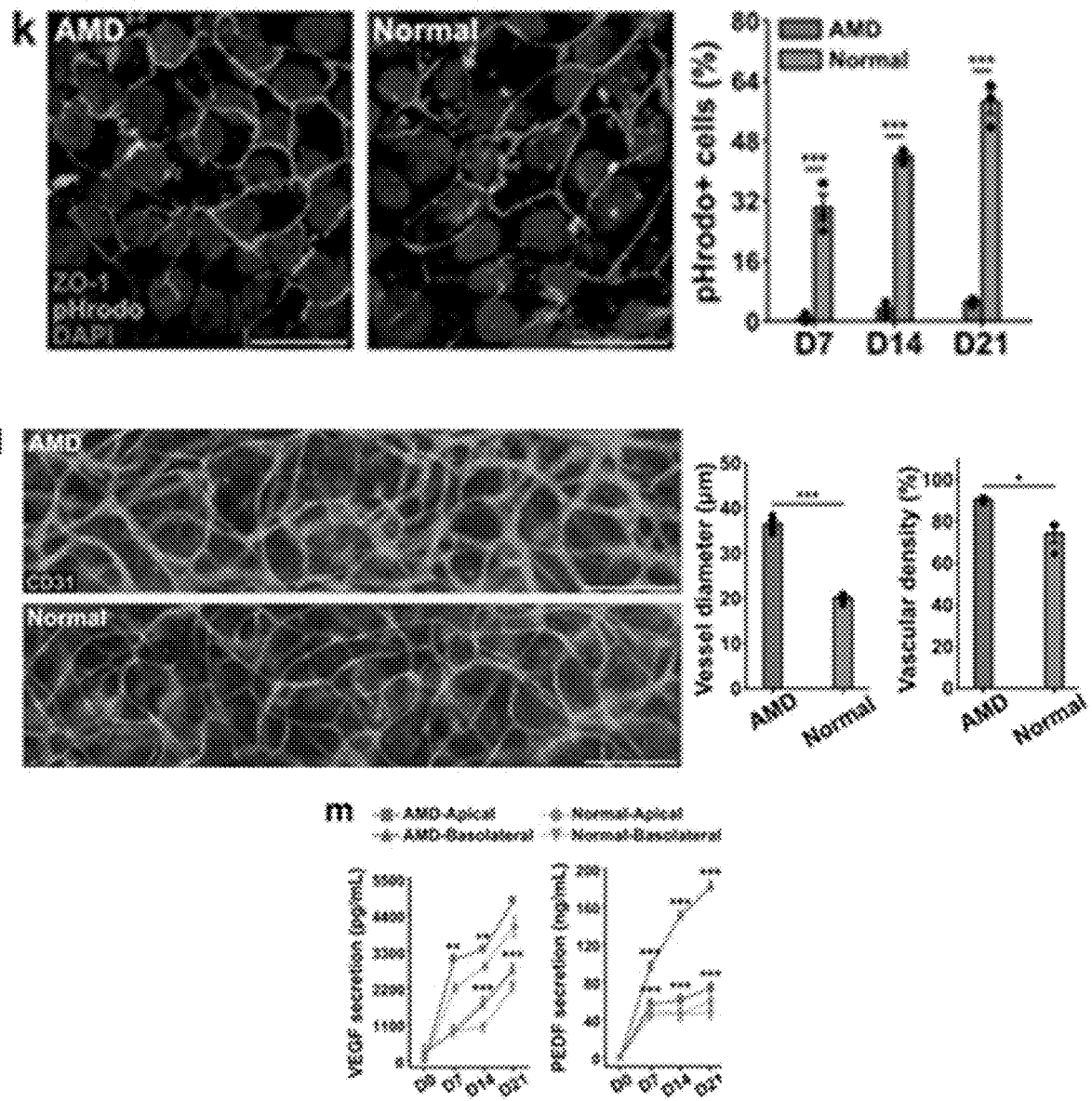
Figures 16A, 16B, 16C, 16D, 16E:
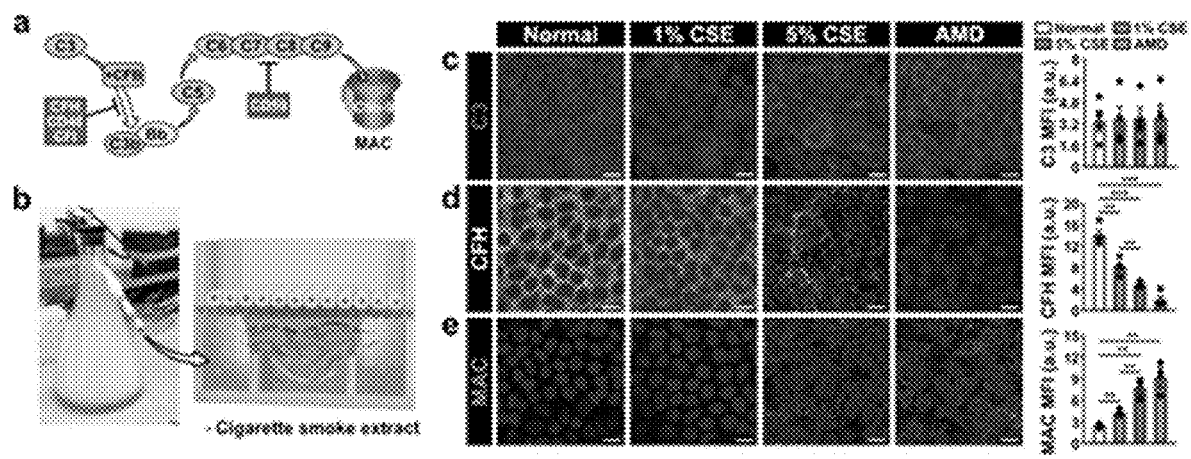
FIGS. 16A-16G illustrated complement activation and efficacy of complement-targeting therapeutic antibodies in a 3D BRB on a chip.
Figure 16F:
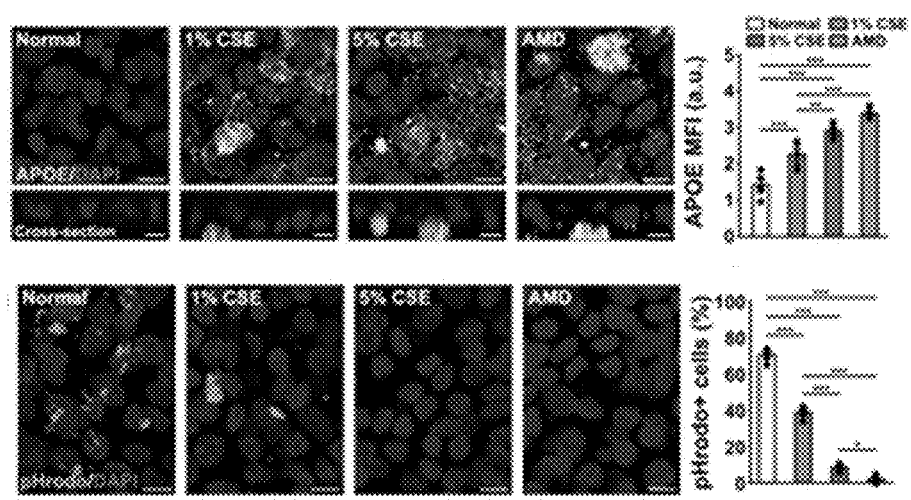
Figure 16G:
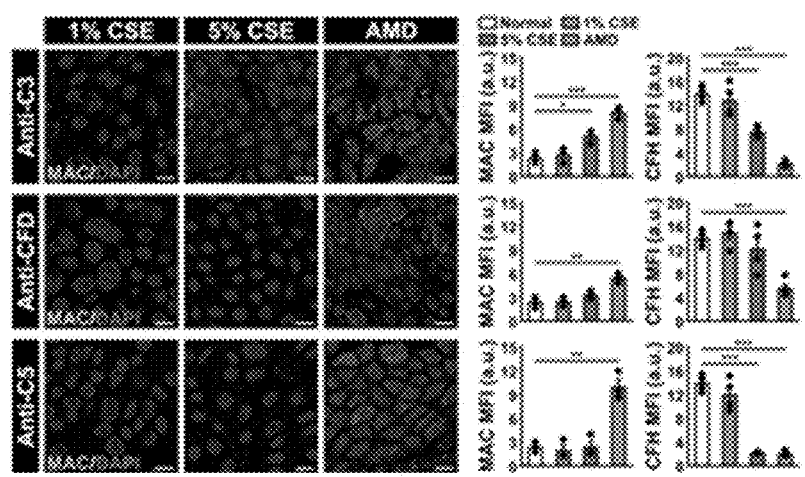

Since the vasculogenesis in ECM hydrogel is affected by the RPEs on top, it was also examined the formation of a microengineered vascular network on BRB chip when cultured with primary or iPS RPEs in the upper chamber. Similar to the primary RPE co-culture, endothelial cells in the vascular chamber self-assembled into a vascular network during the course of a 7-day culture and maintained their structure for more than 21 days (FIG. 14H). Importantly, engineered vessels cultured with iPS-RPEs exhibited similar vessel diameters and densities compared to the primary RPE model, indicating that iPS-derived RPEs do not alter formation of the BRB tissue in this device (FIG. 14H). Another important observation was that both iPS and primary RPE cells produced vascular endothelial growth factor (VEGF) in a similar extent during the course of 21-day culture (FIG. 14I). This demonstrates that the iPS-RPEs in the presently disclosed device have developed into fully differentiated, mature epithelial tissue and are actively involved in paracrine signaling between the RPE and microvasculature. Overall, these results show the ability to microengineer a mature BRB tissue construct using iPS-RPE cells that can be utilized for long-term investigations of the human retina.

All patents, patent applications, publications, product descriptions, and protocols, cited in this specification are hereby incorporated by reference in their entireties. In case of a conflict in terminology, the present disclosure controls.

While it will become apparent that the subject matter herein described is well calculated to achieve the benefits and advantages set forth above, the presently disclosed subject matter is not to be limited in scope by the specific embodiments described herein. It will be appreciated that the disclosed subject matter is susceptible to modification, variation, and change without departing from the spirit thereof. Those skilled in the art will recognize or be able to ascertain using no more than routine experimentation, many equivalents to the specific embodiments described herein. Such equivalents are intended to be encompassed by the following claims.

The invention claimed is:

1. A microfluidic chip for three-dimensional in vitro organoid culture, the microfluidic chip comprising:
   a bottom layer comprising a center lane and at least one side microfluidic channel adjacent thereto, wherein the bottom layer further comprises
   a cell-laden hydrogel within the center lane,
      the at least one side microfluidic channel comprising a luminal surface bearing an endothelium that forms a lumen within the at least one side microfluidic channel;
   a top layer comprising a center reservoir and at least two side reservoirs,
      the center reservoir comprising retinal pigment epithelial cells, and
      the at least two side reservoirs extending through the top layer and into fluid communication with one or more of the at least one side microfluidic channel of the bottom layer; and
   a porous membrane arranged between the bottom layer and the top layer.

2. The microfluidic chip of claim 1, wherein the bottom layer and the top layer comprise polydimethylsiloxane (PDMS).

3. The microfluidic chip of claim 1, wherein the cell-laden hydrogel within the center lane of the bottom layer comprises perfusable vessels.

4. The microfluidic chip of claim 3, wherein the perfusable vessels have a thickness of about 400 µm.

5. The microfluidic chip of claim 1, wherein the center reservoir has a diameter of about 6 mm.

6. The microfluidic chip of claim 1, wherein the retinal pigment epithelial cells are derived from inducible pluripotent stem cells (iPSC).

7. The microfluidic chip of claim 1, wherein the cell-laden hydrogel within the center lane of the bottom layer comprises an extracellular matrix hydrogel.

8. The microfluidic chip of claim 7, wherein the extracellular matrix hydrogel comprises fibrinogen and thrombin.

9. The microfluidic chip of claim 1, wherein the cell-laden hydrogel within the center lane of the bottom layer comprises fibroblasts.

10. The microfluidic chip of claim 1, wherein the cell-laden hydrogel within the center lane of the bottom layer comprises endothelial cells.

11. The microfluidic chip of claim 1, wherein the retinal pigment epithelial cells are derived from a subject.

12. The microfluidic chip of claim 11, wherein the subject has age-related macular degeneration (AMD).

* * * * *

UNITED STATES PATENT AND TRADEMARK OFFICE
CERTIFICATE OF CORRECTION

| | |
|---|---|
| PATENT NO. | : 12,018,279 B2 |
| APPLICATION NO. | : 17/074074 |
| DATED | : June 25, 2024 |
| INVENTOR(S) | : Sunghee Estelle Park et al. |

It is certified that error appears in the above-identified patent and that said Letters Patent is hereby corrected as shown below:

In the Specification

Under Column no. 9, Line no. 1, Replace:
"about 100 In"
With:
--about 100 µm. In--

Under Column no. 14, Line no. 48, Replace:
"radioimmunoassays (MA), enzyme"
With:
--radioimmunoassays (RIA), enzyme--

Signed and Sealed this
Third Day of September, 2024

Katherine Kelly Vidal
*Director of the United States Patent and Trademark Office*